US008399635B2

(12) United States Patent
Baker et al.

(10) Patent No.: US 8,399,635 B2
(45) Date of Patent: Mar. 19, 2013

(54) CHITOSAN DERIVATIVES TO TREAT ANIMALS OR OPTIMIZE ANIMAL HEALTH

(75) Inventors: Shenda Baker, Upland, CA (US); William P. Wiesmann, Washington, DC (US)

(73) Assignee: Synedgen, Inc., Claremont, CA (US)

( * ) Notice: Subject to any disclaimer, the term of this patent is extended or adjusted under 35 U.S.C. 154(b) by 399 days.

(21) Appl. No.: 12/617,349

(22) Filed: Nov. 12, 2009

(65) Prior Publication Data

US 2010/0137193 A1 Jun. 3, 2010

Related U.S. Application Data

(60) Provisional application No. 61/113,981, filed on Nov. 12, 2008.

(51) Int. Cl.
*C08B 37/08* (2006.01)
*A01N 43/04* (2006.01)

(52) U.S. Cl. ........................................ 536/20; 514/55

(58) Field of Classification Search ...................... None
See application file for complete search history.

(56) References Cited

U.S. PATENT DOCUMENTS 6,057,144 A 5/2000 Tokuyasu et al.
8,119,780 B2 * 2/2012 Baker et al. .................... 536/20
2005/0085443 A1 * 4/2005 Chinachoti et al. ............ 514/55
2006/0120973 A1 * 6/2006 Dyer et al. ..................... 424/46
2007/0281904 A1 12/2007 Baker et al.

OTHER PUBLICATIONS

Shiau et al. Chitin but not chitosan supplementation enhances growth of grass shrimp, *Penaeus monodon*. The Journal of Nutrition. 1998, vol. 128, No. 5, pp. 908-912.*

Yalpani et al. Antimicrobial Activity of Some Chitosan Derivatives in: Brine, C. J.; Sandford, P. A. & Zikakis, J. P. (Eds), "Advances in Chitin and Chitosan", Elsevier, London, vol. 1002, p. 543-548.*

Liu et al. A chitosan-arginine conjugate as a novel anticoagulation biomaterial. Journal of Material Science: Material in Medicine. 2004, vol. 15, pp. 1199-1203.*

International Search Report and Written Opinion in corresponding International Application PCT/US2009/064250, 12 pgs., dated Jan. 18, 2010.

Jeon You-Jin et al., "Effect of antimicrobial activity by chitosan oligosaccaride N-conjugated with asparagine", Journal of Microbiology and Biotechnology, Korean Society for Applied Microbiology, Seoul, KR, vol. 11, No. 2, p. 281-286 (Apr. 1, 2001).

Rabea et al., "Chitosan as antimicrobial agent: applications and mode of action", Biomacromolecules, ACS, Washington, DC, vol. 4, No. 6, p. 1457-1465 (Sep. 3, 2003).

* cited by examiner

*Primary Examiner* — Marcela M Cordero Garcia
(74) *Attorney, Agent, or Firm* — Lando & Anastasi LLP

(57) ABSTRACT

Described herein are methods of inhibiting the growth of or killing a bacterium in an animal subject, preventing or delaying onset of an infection with a bacterium in an animal subject, preventing or delaying onset of a pathogen mediated disease or disorder in an animal subject, or reducing bacterial load in an animal subject, comprising administering an effective amount of a derivatized chitosan to the animal. Also described herein are preparations comprising a chitosan derivative for administration to an animal.

15 Claims, 6 Drawing Sheets

CA 10 = 10% functionalized

CA 30 = 30% functionalized

P < 0.05 Statistically sig *

P < 0.10 Numerically sig†

BMD = bacitracin

Non-med >> 100ppm/10ppm >> BMD

Weight gain (14d post infection) in kg difference of 0.05 has financial impact

BMD >> 100ppm >> nonmed/10ppm (statistically significant groups)

CHITOSAN DERIVATIVES TO TREAT ANIMALS OR OPTIMIZE ANIMAL HEALTH

PRIORITY CLAIM

The present application claims the benefit of U.S. provisional application No. 61/113,981, filed Nov. 12, 2008, the contents of which are incorporated herein by reference.

FIELD OF THE INVENTION

The invention relates to the use of chitosan derivatives, e.g., to treat or inhibit infections, or generally optimize animal health, e.g., to optimize weight gain to allow for the use of lower doses of anti-bacterial agents.

BACKGROUND

Animal diseases, especially those that afflict animals used for the production of food or fiber, result in tremendous economic loss and human suffering.

SUMMARY OF THE INVENTION

Chitosan derivatives are described. The derivatized chitosan can be used to optimize animal health, e.g., to optimize weight gain to allow for the use of lower doses of anti-bacterial agents.

In one aspect, the invention features a method of inhibiting the growth of a bacterium and/or killing a bacterium in an animal subject, preventing or delaying onset of an infection with a bacterium in an animal subject, preventing or delaying onset of a pathogen mediated disease or disorder in an animal subject, or reducing bacterial load in an animal subject. The method includes administering an effective amount of a derivatized chitosan to said animal, thereby inhibiting the growth of a bacterium and/or killing a bacterium in an animal subject, preventing or delaying onset of an infection with a bacterium in an animal subject, preventing or delaying onset of a pathogen mediated disease or disorder in an animal subject, or reducing bacterial load in an animal subject, in an animal subject.

In some embodiments, the derivatized chitosan is administered orally, e.g., in the subject's feed or water.

In some embodiments, the derivatized chitosan is administered by inhalation.

In some embodiments, the derivatized chitosan is soluble in aqueous solution from about pH 6.8 to about pH 7.4.

In some embodiments, the derivatized chitosan is soluble in aqueous solution from about pH 3 to about pH 9.

In some embodiments, the derivatized chitosan comprises a chitosan of the following formula (I):

formula (I)

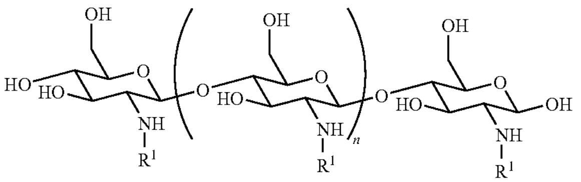

wherein:

n is an integer between 20 and 6000; and each $R^1$ is independently selected for each occurrence from hydrogen, acetyl, and either:

a) a group of formula (II):

formula (II)

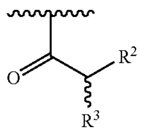

wherein $R^2$ is hydrogen or amino; and $R^3$ is amino, guanidino, $C_1$-$C_6$ alkyl substituted with an amino or guanidino moiety, or a natural or unnatural amino acid side chain;

or b) $R^1$, when taken together with the nitrogen to which it is attached, forms a guanidine moiety;

wherein at least 25% of $R^1$ substituents are H, at least 1% of $R^1$ substituents are acetyl, and at least 2% of $R^1$ substituents are a group of formula (II) or are taken together with the nitrogen to which they are attached to form a guanidine moiety.

In some embodiments, between 25-95% of $R^1$ substituents are hydrogen.

In some embodiments, between 55-90% of $R^1$ substituents are hydrogen.

In some embodiments, between 1-50% of $R^1$ substituents are acetyl.

In some embodiments, between 4-20% of $R^1$ substituents are acetyl.

In some embodiments, between 2-50% of $R^1$ substituents are a group of formula (II).

In some embodiments, between 4-30% of $R^1$ substituents are a group of formula (II).

In some embodiments, 55-90% of $R^1$ substituents are hydrogen, 4-20% of $R^1$ substituents are acetyl, 4-30% of $R^1$ substituents are a group of formula (II).

In some embodiments, $R^2$ is amino and $R^3$ is an arginine side chain.

In some embodiments, $R^1$ is selected from one of the following:

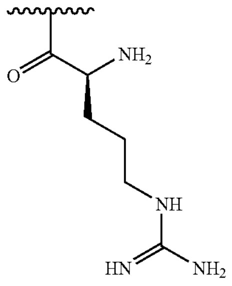

and

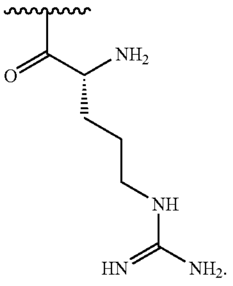

In some embodiments, $R^2$ is amino and $R^3$ is a lysine side chain.

In some embodiments, $R^1$ is selected from one of the following:

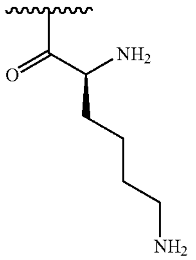 and 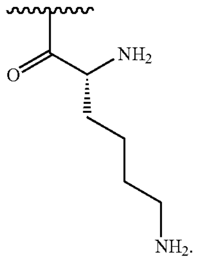

In some embodiments, $R^2$ is amino and $R^3$ is a histidine side chain.

In some embodiments, $R^1$ is selected from one of the following:

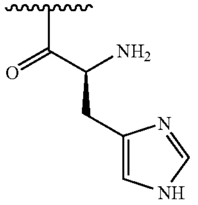 and 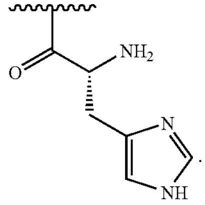

In some embodiments, at least 1% of $R^1$ substituents are selected from one of the following:

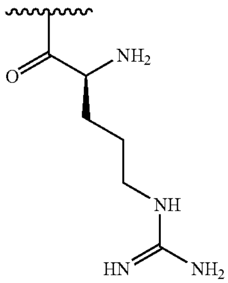 and 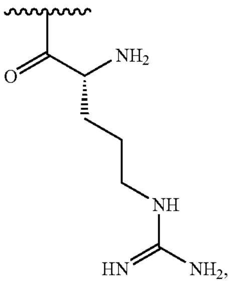

AND at least 1% of $R^1$ substituents are selected from the following:

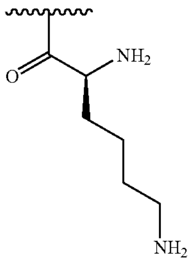 and 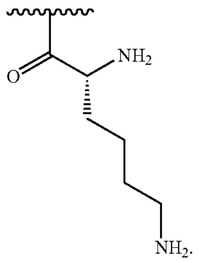

In some embodiments, $R^2$ is amino and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^1$ is selected from one of the following:

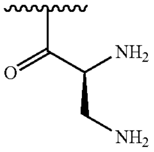
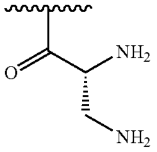
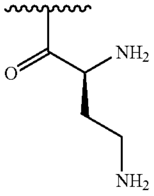
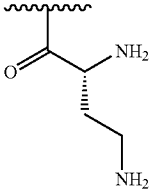
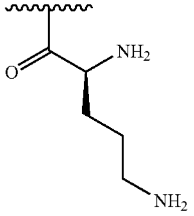
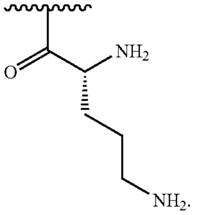

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^1$ is selected from one of the following:

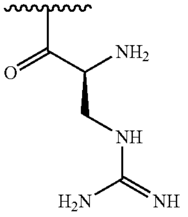
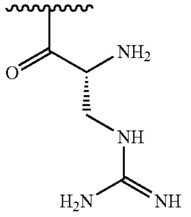
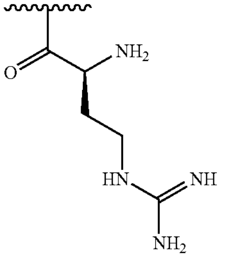
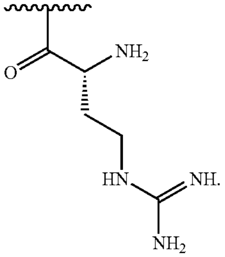

In some embodiments, $R^2$ is amino that is substituted with a nitrogen protecting group prior to substitution on chitosan and removed subsequent to substitution on chitosan.

In some embodiments, the nitrogen protecting group is tert-butyloxycarbonyl (Boc).

In some embodiments, in the synthetic process a nitrogen protecting group is used, which can provide an intermediate polymer having a nitrogen protecting group such as Boc.

In some embodiments, $R^2$ is amino.

In some embodiments, $R^2$ is hydrogen and $R^3$ is amino.

In some embodiments, $R^2$ is hydrogen and $R^3$ is guanidino.

In some embodiments, $R^2$ is hydrogen and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^3$ is $C_4$ alkyl substituted with an amino group.

In some embodiments, $R^3$ is $C_5$ alkyl substituted with an amino group.

In some embodiments, $R^1$ is selected from one of the following:

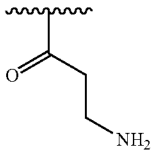
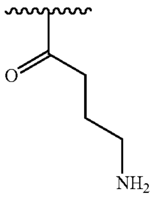
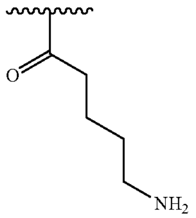
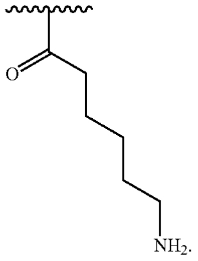

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^3$ is $C_3$ alkyl substituted with a guanidino group.

In some embodiments, $R^1$ is selected from one of the following:

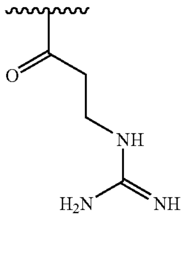
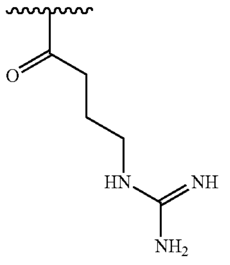

-continued

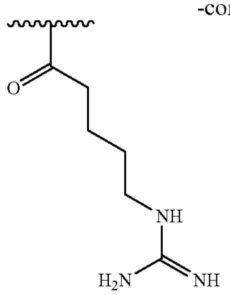
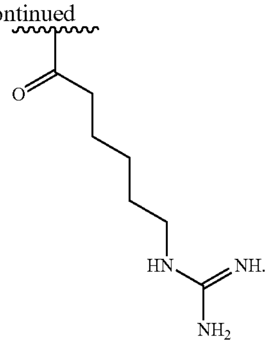

In some embodiments, at least 25% of $R^1$ substituents are H, at least 1% of $R^1$ substituents are acetyl, and at least 2% of $R^1$ substituents independently selected from any of the formulae specifically shown above.

In some embodiments, the chitosan of formula (I) may be further derivatized on the free hydroxyl moieties.

In some embodiments, the molecular weight of the derivatized chitosan is between 5,000 and 1,000,000 Da.

In some embodiments, the molecular weight of the derivatized chitosan is between 5,000 and 350,000 Da.

In some embodiments, the molecular weight of the derivatized chitosan is between 10,000 and 150,000 Da.

In some embodiments, the molecular weight of the derivatized chitosan is between 15,000 and 100,000 Da.

In some embodiments, the molecular weight of the derivatized chitosan is between 20,000 and 30,000 Da.

In some embodiments, the chitosan is functionalized at between 5% and 50%.

In a preferred embodiment, the chitosan is functionalized at between 20% and 30%.

In some embodiments, the degree of deacetylation (% DDA) of the derivatized chitosan is between 75% and 95%.

In some embodiments, the degree of deacetylation (% DDA) of the derivatized chitosan is between 80% and 90%.

In some embodiments, the polydispersity index (PDI) of the derivatized chitosan is between 1.0 and 2.5.

In some embodiments, the polydispersity index (PDI) of the derivatized chitosan is between 1.5 and 2.0.

In some embodiments, the derivatized chitosan is substantially free of other impurities, e.g., salt, e.g., NaCl.

In some embodiments, the bacterium is selected from the group consisting of Gram-negative and Gram-positive bacteria.

In some embodiments, the method also includes administering to the animal subject an anti-bacterial agent. In some embodiments, the anti-bacterial agent is selected from the group consisting of Gram-positive, Gram-negative, and broad spectrum antibiotic. In some embodiments, the anti-bacterial agent is selected from the group consisting of aminoglycosides, beta-lactam antibiotics, macrolides, antibiotic polypeptides, antibiotic lipopeptides, antibiotic glycopeptides, monobactams, quinolones, sulfonamides and tetracyclines.

In some embodiments, the animal subject is a pig, sheep, cow, goat, chicken, turkey, duck or goose.

In some embodiments, the infection is a *Colibacillosis* infection, e.g., an *Escherichia coli* infection.

In some embodiments, the animal subject has a respiratory disease, e.g., from air sac infection, a septicemic (blood) disease from generalized infections, an enteritis from intestinal infection, or a combination of any or all of these conditions. In some embodiments, the disease results from a coliform infection alone as in primary infection or in combination with other disease agents as a complicating or secondary infection. In some embodiments, the secondary infection is a *Mycoplasma gallisepticum* infection. In some embodiments, the animal subject is a turkey or chicken, e.g., a young chicken or turkey. In some embodiments, the animal subject has a navel infection.

In some embodiments, the disease is *Coccidiosis*. In some embodiments, the disease is coccidian infection. In some embodiments, the disease or disorder is diarrhea. In some embodiments, the disease is fowl cholera. In some embodiments, the animal subject is a chicken, turkey, pheasant, pigeon, waterfowl, sparrow and or other free-flying bird. In some embodiments, the animal subject has a *Pasteurella multocida* infection. In some embodiments, the disease is infectious bronchitis. In some embodiments, the animal subject is a chicken. In some embodiments, the disease is necrotic enteritis. In some embodiments, the animal subject is a bird. In some embodiments, the animal subject has a *Clostridium perfringens* infection.

In some embodiments, the animal subject is also administered an anti-bacterial agent, e.g., in the case of a *Clostridium perfringens* infection, bacitracin or virginiamycin.

In some embodiments, the anti-bacterial agent and derivatized chitosan are present at a concentration, or administered at a dose, which results in a synergistic effect, e.g., the inhibition is greater, e.g., at least 2, 4, 10, 20, 50, or 100 times greater, than the sum of the inhibition seen with either used alone. In some embodiments, the anti-bacterial agent is present at a concentration, or administered at a dose, which is less than the lowest concentration, or dose, that would give maximum inhibition in the absence of the derivatized chitosan. In some embodiments, the anti-bacterial agent is present at a concentration, or administered at a dose, which is less than the lowest concentration, or dose, generally used to treat infections of the bacterium. In some embodiments, the anti-bacterial agent is present at a concentration, or administered at a dose, which is less than 90, 80, 70, 60, 50, 40, 30, 20, 10, 5, 1, 0.1, 0.01% of the lowest concentration, or dose, that would give maximum inhibition in the absence of the derivatized chitosan. In some embodiments, the anti-bacterial agent is present at a concentration, or administered at a dose, which is less than 90, 80, 70, 60, 50, 40, 30, 20, 10, 5, 1, 0.1, 0.01% of the lowest concentration, or dose, generally used to treat infections of the bacterium. In some embodiments, the anti-bacterial agent and derivatized chitosan are present at a concentration, or administered at a dose, which are lower than the MIC of at least one of the anti-bacterial agent or derivatized chitosan when administered in the abasence the other. In some embodiments, the anti-bacterial agent and derivatized chitosan are present at a concentration, or administered at a dose, which have an FIC less than about 0.5, 0.4, 0.3, 0.2, 0.1, 0.05, or 0.01. In some embodiments, the anti-bacterial agent is present at a concentration, or administered at a dose, which would not result in substantial inhibition of bacterial growth in the absence of the derivatized chitosan. In some embodiments, the anti-bacterial agent is present at a concentration, or administered at a dose, which would not result in clinical or therapeutic levels of inhibition of bacterial growth in the absence of the derivatized chitosan.

In some embodiments, the animal subject is also administered a vitamin treatment.

In some embodiments, the disease is acute or chronic ulcerative enteritis. In some embodiments, the animal subject is a bird, e.g., a quail, bird, chicken, turkey or other domestic fowl. In some embodiments, the animal subject has a *Clostridium colinum* infection.

In some embodiments, the infection or disorder has previously been treated with an anti-bacterial agent without a chitosan derivative and, e.g., said treatment was unsatisfactory.

In one aspect, the invention features a preparation of animal feed comprising feed and a chitosan derivative. In some embodiments, the preparation also includes an anti-bacterial agent. In another aspect, the invention features the chitosan-derivative dissolved in the water available to the animal. In some embodiments, the anti-bacterial agent is selected from the group consisting of Gram-positive, Gram-negative, and broad spectrum antibiotic. In some embodiments, the antibiotic is selected from the group consisting of aminoglycosides, beta-lactam antibiotics, macrolides, antibiotic polypeptides, antibiotic lipopeptides, antibiotic glycopeptides, monobactams, quinolones, sulfonamides and tetracyclines.

In some embodiments, the derivatized chitosan is soluble in aqueous solution from about pH 6.8 to about pH 7.4.

In some embodiments, the derivatized chitosan is soluble in aqueous solution from about pH 3 to about pH 9.

In some embodiments, the derivatized chitosan is soluble in aqueous solution from about pH 5.0 to about pH 6.0, e.g., in wounds or duodenum.

In some embodiments, the derivatized chitosan is soluble in aqueous solution from about pH 2.0 to about pH 4.0, e.g., in stomach.

In some embodiments, the derivatized chitosan is soluble in aqueous solution from about pH 8.0 to about pH 8.5, e.g., in lower part of the gastrointestinal tract.

In some embodiments, the derivatized chitosan comprises a chitosan of the following formula (I):

formula (I)

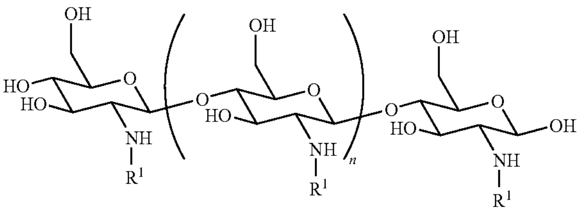

wherein:

n is an integer between 20 and 6000; and each $R^1$ is independently selected for each occurrence from hydrogen, acetyl, and either:

a) a group of formula (II):

formula (II)

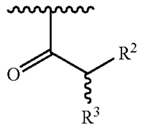

wherein $R^2$ is hydrogen or amino; and $R^3$ is amino, guanidino, $C_1$-$C_6$ alkyl substituted with an amino or guanidino moiety, or a natural or unnatural amino acid side chain;

or b) $R^1$, when taken together with the nitrogen to which it is attached, forms a guanidine moiety;

wherein at least 25% of $R^1$ substituents are H, at least 1% of $R^1$ substituents are acetyl, and at least 2% of $R^1$ substituents are a group of formula (II) or are taken together with the nitrogen to which they are attached to form a guanidine moiety.

In some embodiments, between 25-95% of $R^1$ substituents are hydrogen.

In some embodiments, between 55-90% of $R^1$ substituents are hydrogen.

In some embodiments, between 1-50% of $R^1$ substituents are acetyl.

In some embodiments, between 4-20% of $R^1$ substituents are acetyl.

In some embodiments, between 2-50% of $R^1$ substituents are a group of formula (II).

In some embodiments, between 4-30% of $R^1$ substituents are a group of formula (II).

In some embodiments, 55-90% of $R^1$ substituents are hydrogen, 4-20% of $R^1$ substituents are acetyl, 4-30% of $R^1$ substituents are a group of formula (II).

In some embodiments, $R^2$ is amino and $R^3$ is an arginine side chain.

In some embodiments, $R^1$ is selected from one of the following:

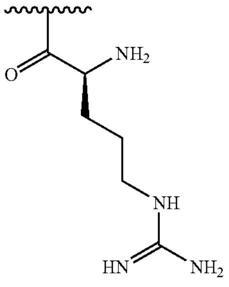
and
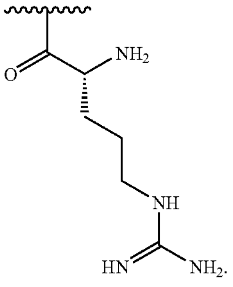

In some embodiments, $R^2$ is amino and $R^3$ is a lysine side chain.

In some embodiments, $R^1$ is selected from one of the following:

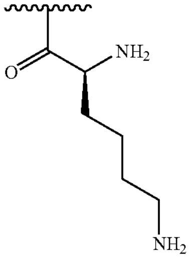
and
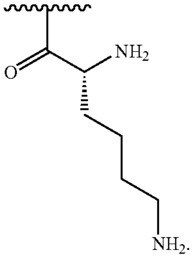

In some embodiments, $R^2$ is amino and $R^3$ is a histidine side chain.

In some embodiments, $R^1$ is selected from one of the following:

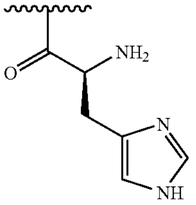
and
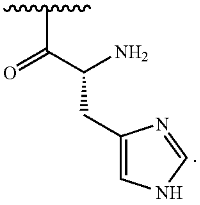

In some embodiments, at least 1% of $R^1$ substituents are selected from one of the following:

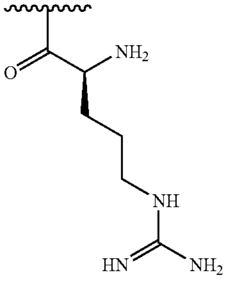
and
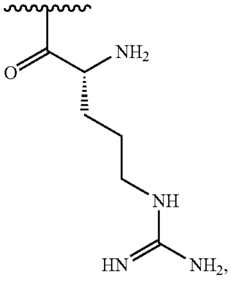

AND at least 1% of $R^1$ substituents are selected from the following:

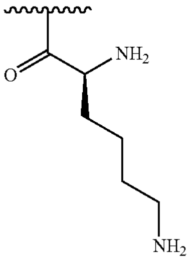
and
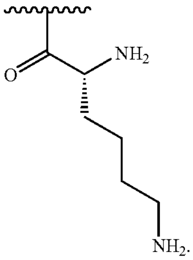

In some embodiments, $R^2$ is amino and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^1$ is selected from one of the following:

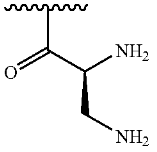
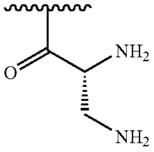
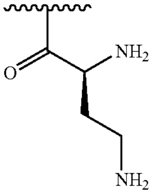

-continued

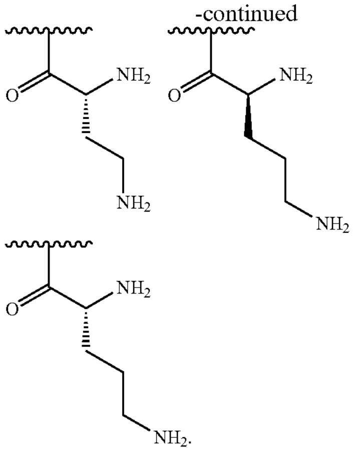

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^1$ is selected from one of the following:

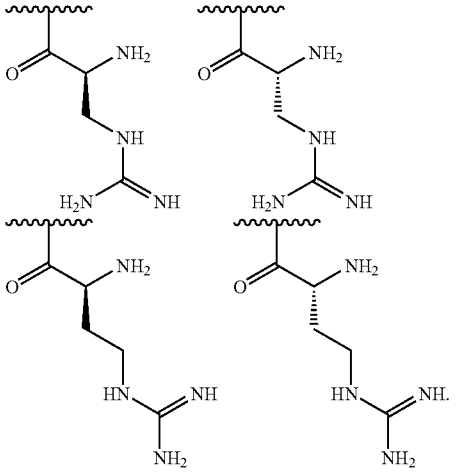

In some embodiments, $R^2$ is amino that is substituted with a nitrogen protecting group prior to substitution on chitosan and removed subsequent to substitution on chitosan.

In some embodiments, the nitrogen protecting group is tert-butyloxycarbonyl (Boc).

In some embodiments, in the synthetic process a nitrogen protecting group is used, which can provide an intermediate polymer having a nitrogen protecting group such as Boc.

In some embodiments, $R^2$ is amino.

In some embodiments, $R^2$ is hydrogen and $R^3$ is amino.

In some embodiments, $R^2$ is hydrogen and $R^3$ is guanidino.

In some embodiments, $R^2$ is hydrogen and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^3$ is $C_4$ alkyl substituted with an amino group.

In some embodiments, $R^3$ is $C_5$ alkyl substituted with an amino group.

In some embodiments, $R^1$ is selected from one of the following:

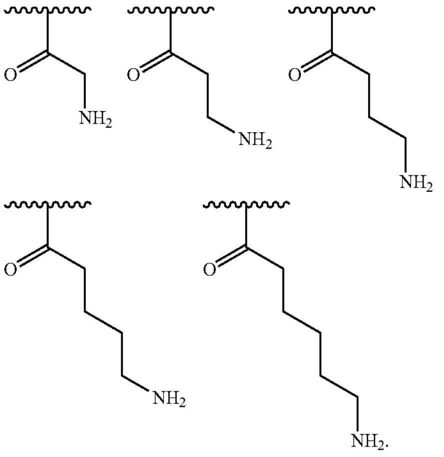

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^3$ is $C_3$ alkyl substituted with a guanidino group.

In some embodiments, $R^3$ is $C_4$ alkyl substituted with a guanidino group.

In some embodiments, $R^3$ is $C_5$ alkyl substituted with a guanidino group.

In some embodiments, $R^1$ is selected from one of the following:

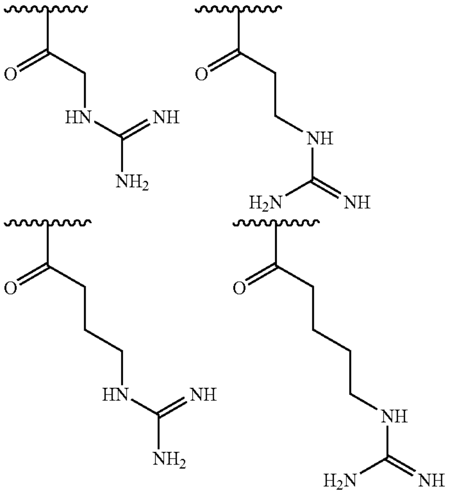

-continued

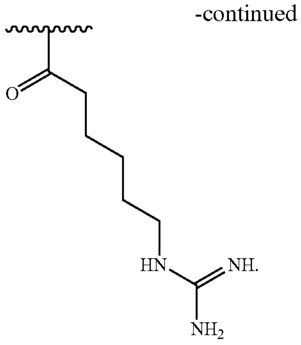

In some embodiments, at least 25% of $R^1$ substituents are H, at least 1% of $R^1$ substituents are acetyl, and at least 2% of $R^1$ substituents independently selected from any of the formulae specifically shown above.

In some embodiments, the chitosan of formula (I) may be further derivatized on the free hydroxyl moieties.

In some embodiments, the molecular weight of the derivatized chitosan is between 5,000 and 1,000,000 Da.

In some embodiments, the molecular weight of the derivatized chitosan is between 5,000 and 350,000 Da.

In some embodiments, the molecular weight of the derivatized chitosan is between 10,000 and 150,000 Da.

In some embodiments, the molecular weight of the derivatized chitosan is between 15,000 and 100,000 Da.

In some embodiments, the molecular weight of the derivatized chitosan is between 20,000 and 30,000 Da.

In some embodiments, the chitosan is functionalized at between 5% and 50%.

In a preferred embodiment, the chitosan is functionalized at between 20% and 30%.

In some embodiments, the degree of deacetylation (% DDA) of the derivatized chitosan is between 75% and 95%.

In some embodiments, the degree of deacetylation (% DDA) of the derivatized chitosan is between 80% and 90%.

In some embodiments, the polydispersity index (PDI) of the derivatized chitosan is between 1.0 and 2.5.

In some embodiments, the polydispersity index (PDI) of the derivatized chitosan is between 1.5 and 2.0.

In some embodiments, the derivatized chitosan is substantially free of other impurities, e.g., salt, e.g., NaCl.

In one aspect, the invention features a method of optimizing weight gain in an animal subject, or in general, optimizing health in an animal subject, comprising:

administering an effective amount of a derivatized chitosan to said animal, thereby optimizing weight gain in an animal subject, or in general, optimizing health in an animal subject.

In some embodiments, the method includes improving and/or optimizing feed conversion. In some embodiments, the method includes improving and/or optimizing animal performance. In some embodiments, the method includes improving and/or optimizing weight gain.

In some embodiments, the method also includes administering to the animal an anti-bacterial agent. In some embodiments, the anti-bacterial agent is selected from the group consisting of Gram-positive, Gram-negative, and broad spectrum antibiotic. In some embodiments, the anti-bacterial agent is selected from the group consisting of aminoglycosides, beta-lactam antibiotics, macrolides, antibiotic polypeptides, antibiotic lipopeptides, antibiotic glycopeptides, monobactams, quinolones, sulfonamides and tetracyclines. In some embodiments, the anti-bacterial agent and chitosan derivative act synergistically.

In some embodiments, the anti-bacterial agent and derivatized chitosan are present at a concentration, or administered at a dose, which results in a synergistic effect, e.g., the inhibition is greater, e.g., at least 2, 4, 10, 20, 50, or 100 times greater, than the sum of the inhibition seen with either used alone. In some embodiments, the anti-bacterial agent is present at a concentration, or administered at a dose, which is less than the lowest concentration, or dose, that would give maximum inhibition in the absence of the derivatized chitosan. In some embodiments, the anti-bacterial agent is present at a concentration, or administered at a dose, which is less than the lowest concentration, or dose, generally used to treat infections of the bacterium. In some embodiments, the anti-bacterial agent is present at a concentration, or administered at a dose, which is less than 90, 80, 70, 60, 50, 40, 30, 20, 10, 5, 1, 0.1, 0.01% of the lowest concentration, or dose, that would give maximum inhibition in the absence of the derivatized chitosan. In some embodiments, the anti-bacterial agent is present at a concentration, or administered at a dose, which is less than 90, 80, 70, 60, 50, 40, 30, 20, 10, 5, 1, 0.1, 0.01% of the lowest concentration, or dose, generally used to treat infections of the bacterium. In some embodiments, the anti-bacterial agent and derivatized chitosan are present at a concentration, or administered at a dose, which are lower than the MIC of at least one of the anti-bacterial agent or derivatized chitosan when administered in the abasence the other. In some embodiments, the anti-bacterial agent and derivatized chitosan are present at a concentration, or administered at a dose, which have an FIC less than about 0.5, 0.4, 0.3, 0.2, 0.1, 0.05, or 0.01. In some embodiments, the anti-bacterial agent is present at a concentration, or administered at a dose, which would not result in substantial inhibition of bacterial growth in the absence of the derivatized chitosan. In some embodiments, the anti-bacterial agent is present at a concentration, or administered at a dose, which would not result in clinical or therapeutic levels of inhibition of bacterial growth in the absence of the derivatized chitosan.

In some embodiments, the derivatized chitosan is soluble in aqueous solution from about pH 6.8 to about pH 7.4.

In some embodiments, the derivatized chitosan is soluble in aqueous solution from about pH 3 to about pH 9.

In some embodiments, the derivatized chitosan is soluble in aqueous solution from about pH 5.0 to about pH 6.0, e.g., in wounds or duodenum.

In some embodiments, the derivatized chitosan is soluble in aqueous solution from about pH 2.0 to about pH 4.0, e.g., in stomach.

In some embodiments, the derivatized chitosan is soluble in aqueous solution from about pH 8.0 to about pH 8.5, e.g., in lower part of the gastrointestinal tract.

In some embodiments, the derivatized chitosan comprises a chitosan of the following formula (I):

formula (I)

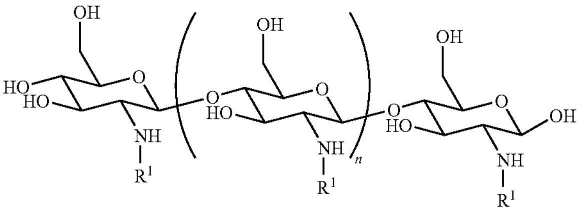

wherein:

n is an integer between 20 and 6000; and each $R^1$ is independently selected for each occurrence from hydrogen, acetyl, and either:

a) a group of formula (II):

formula (II)

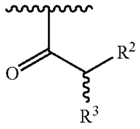

wherein $R^2$ is hydrogen or amino; and $R^3$ is amino, guanidino, $C_1$-$C_6$ alkyl substituted with an amino or guanidino moiety, or a natural or unnatural amino acid side chain;

or b) $R^1$, when taken together with the nitrogen to which it is attached, forms a guanidine moiety;

wherein at least 25% of $R^1$ substituents are H, at least 1% of $R^1$ substituents are acetyl, and at least 2% of $R^1$ substituents are a group of formula (II) or are taken together with the nitrogen to which they are attached to form a guanidine moiety.

In some embodiments, between 25-95% of $R^1$ substituents are hydrogen.

In some embodiments, between 55-90% of $R^1$ substituents are hydrogen.

In some embodiments, between 1-50% of $R^1$ substituents are acetyl.

In some embodiments, between 4-20% of $R^1$ substituents are acetyl.

In some embodiments, between 2-50% of $R^1$ substituents are a group of formula (II).

In some embodiments, between 4-30% of $R^1$ substituents are a group of formula (II).

In some embodiments, 55-90% of $R^1$ substituents are hydrogen, 4-20% of $R^1$ substituents are acetyl, 4-30% of $R^1$ substituents are a group of formula (II).

In some embodiments, $R^2$ is amino and $R^3$ is an arginine side chain.

In some embodiments, $R^1$ is selected from one of the following:

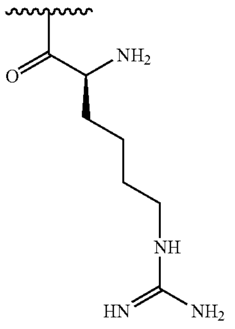

and

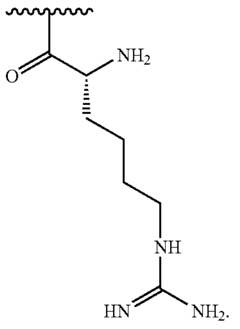

In some embodiments, $R^2$ is amino and $R^3$ is a lysine side chain.

In some embodiments, $R^1$ is selected from one of the following:

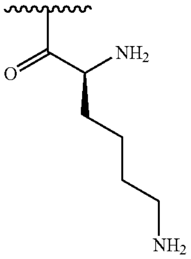

and

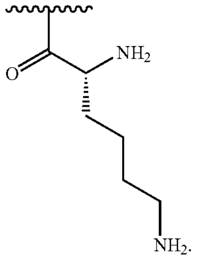

In some embodiments, $R^2$ is amino and $R^3$ is a histidine side chain.

In some embodiments, $R^1$ is selected from one of the following:

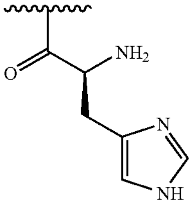

and

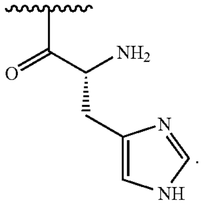

In some embodiments, at least 1% of $R^1$ substituents are selected from one of the following:

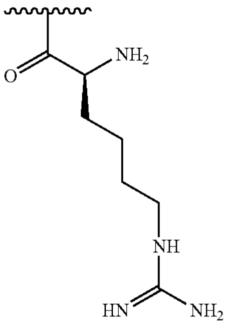

and

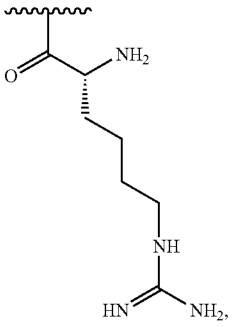

AND at least 1% of $R^1$ substituents are selected from the following:

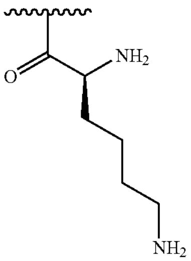

and

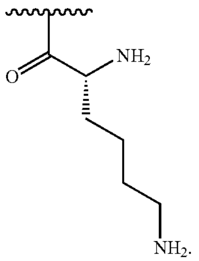

In some embodiments, $R^2$ is amino and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^1$ is selected from one of the following:

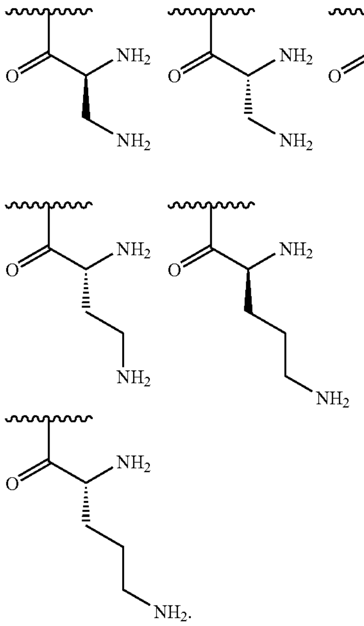

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^1$ is selected from one of the following:

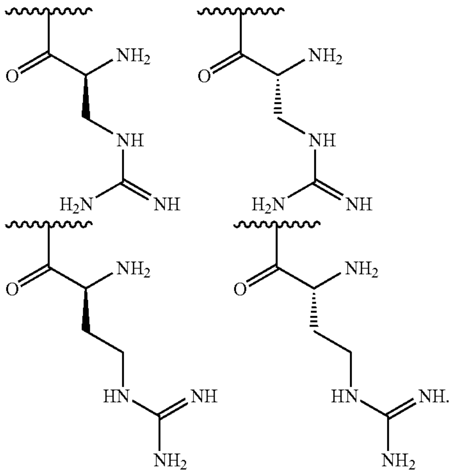

In some embodiments, $R^2$ is amino that is substituted with a nitrogen protecting group prior to substitution on chitosan and removed subsequent to substitution on chitosan.

In some embodiments, the nitrogen protecting group is tert-butyloxycarbonyl (Boc).

In some embodiments, in the synthetic process a nitrogen protecting group is used, which can provide an intermediate polymer having a nitrogen protecting group such as Boc.

In some embodiments, $R^2$ is amino.

In some embodiments, $R^2$ is hydrogen and $R^3$ is amino.

In some embodiments, $R^2$ is hydrogen and $R^3$ is guanidino.

In some embodiments, $R^2$ is hydrogen and $R^3$ is a substituted $C_1$-$C_6$ alkyl.

In some embodiments, $R^3$ is $C_1$-$C_6$ alkyl substituted with an amino group.

In some embodiments, $R^3$ is $C_1$ alkyl substituted with an amino group.

In some embodiments, $R^3$ is $C_2$ alkyl substituted with an amino group.

In some embodiments, $R^3$ is $C_3$ alkyl substituted with an amino group.

In some embodiments, $R^3$ is $C_4$ alkyl substituted with an amino group.

In some embodiments, $R^3$ is $C_5$ alkyl substituted with an amino group.

In some embodiments, $R^1$ is selected from one of the following:

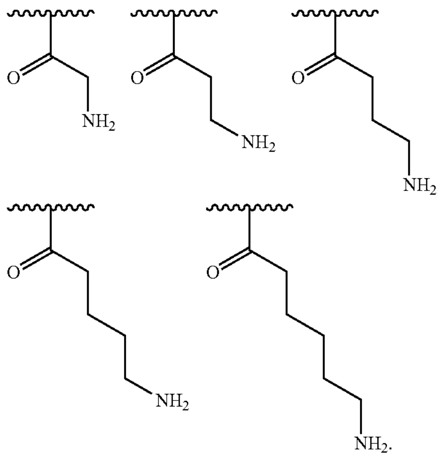

In some embodiments, $R^3$ is $C_1$-$C_6$ alkyl substituted with a guanidino group.

In some embodiments, $R^3$ is $C_1$ alkyl substituted with a guanidino group.

In some embodiments, $R^3$ is $C_2$ alkyl substituted with a guanidino group.

In some embodiments, $R^3$ is $C_3$ alkyl substituted with a guanidino group.

In some embodiments, $R^3$ is $C_4$ alkyl substituted with a guanidino group.

In some embodiments, $R^3$ is $C_5$ alkyl substituted with a guanidino group.

In some embodiments, $R^1$ is selected from one of the following:

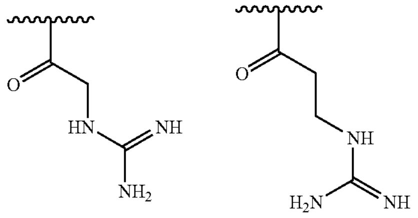

-continued

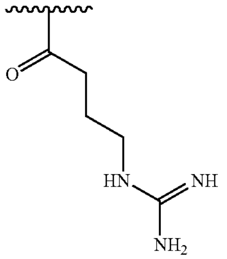

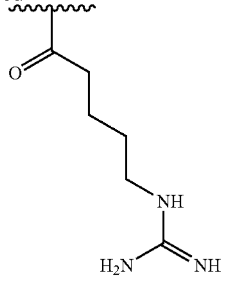

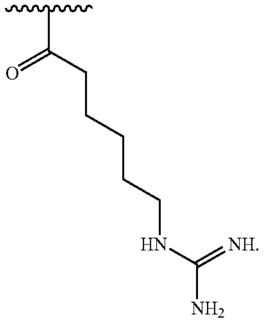

In some embodiments, at least 25% of $R^1$ substituents are H, at least 1% of $R^1$ substituents are acetyl, and at least 2% of $R^1$ substituents independently selected from any of the formulae specifically shown above.

In some embodiments, the chitosan of formula (I) may be further derivatized on the free hydroxyl moieties.

In some embodiments, the molecular weight of the derivatized chitosan is between 5,000 and 1,000,000 Da.

In some embodiments, the molecular weight of the derivatized chitosan is between 5,000 and 350,000 Da.

In some embodiments, the molecular weight of the derivatized chitosan is between 10,000 and 150,000 Da.

In some embodiments, the molecular weight of the derivatized chitosan is between 15,000 and 100,000 Da.

In some embodiments, the molecular weight of the derivatized chitosan is between 20,000 and 30,000 Da.

In some embodiments, the chitosan is functionalized at between 5% and 50%.

In a preferred embodiment, the chitosan is functionalized at between 20% and 30%.

In some embodiments, the degree of deacetylation (% DDA) of the derivatized chitosan is between 75% and 95%.

In some embodiments, the degree of deacetylation (% DDA) of the derivatized chitosan is between 80% and 90%.

In some embodiments, the polydispersity index (PDI) of the derivatized chitosan is between 1.0 and 2.5.

In some embodiments, the polydispersity index (PDI) of the derivatized chitosan is between 1.5 and 2.0.

In some embodiments, the derivatized chitosan is substantially free of other impurities, e.g., salt, e.g., NaCl.

DETAILED DESCRIPTION

Overview

Figure 1:
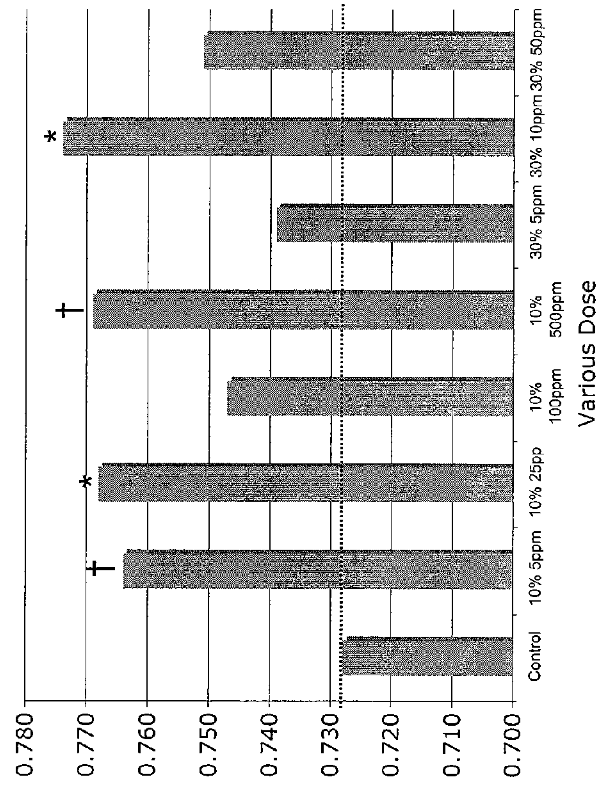
FIG. 1 depicts the effect of chitosan-arginine delivered in feed on weight gain in poultry study.

Described herein are compositions and methods useful for inhibiting the growth of a bacterium and/or killing a bacterium in an animal subject, preventing or delaying onset of an infection with a bacterium in an animal subject, methods of preventing or delaying onset of a pathogen mediated disease or disorder in an animal subject, and methods of minimizing or reducing bacterial load in an animal subject, in an animal subject. Also described herein are methods of optimizing weight gain in an animal subject, or in general, optimizing health of an animal by administering to an animal a chitosan derivative described herein (e.g., alone or in combination with another agent such as an anti-bacterial agent). In some embodiments, for example, in embodiments where the chitosan derivative is used in combination with another agent, the agents act synergistically.

Methods disclosed herein allow achieving these aims with or without the administration of anti-bacterial agents to animals, or in some cases, greatly reduce the amount of an anti-bacterial agent needed. These methods include administering to a subject a chitosan derivative described herein. In some embodiments, the subject has a bacterial infection, e.g., the chitosan derivative is administered to the subject to treat the bacterial infection or reduce bacterial load. In some embodiments, the subject does not have a bacterial infection, e.g., the chitosan derivative is administered as a prophylactic or to otherwise optimize the weight and/or health of the subject.

The chitosan derivatives can be administered as described herein, for example administered in a formulation described herein such as a feed or feed supplement. In some embodiments, the chitosan derivative is administered together with another agent such as an anti-bacterial agent. Weight gain is often measured as a weight to feed conversion. Optimizing weight gain is the process of improving the amount of weight an animal gains for a given amount of feed. Optimized animal health reflects the overall tendency of the flock, herd or collection of animals to succumb to bacterial infections. Statistically, animals in optimal health have few to no bacterial infections that must be treated.

Treatment

The compounds described herein can be administered to a subject, e.g., in vivo, to treat or prevent a variety of disorders, including those described herein below.

As used herein, the term "treat" or "treatment" is defined as the application or administration of a compound (e.g., a combination of compounds described herein) to a subject, e.g., an animal, or application or administration of the compound to an isolated tissue or cell, e.g., cell line, from a subject, e.g., an animal, who has a bacterial disorder (e.g., a bacterial infection), a symptom of a bacterial disorder, or a predisposition toward a bacterial disorder, with the purpose to cure, heal, alleviate, relieve, alter, remedy, ameliorate, improve or affect the bacterial disorder, one or more symptoms of the bacterial disorder or the predisposition toward the bacterial disorder (e.g., to prevent at least one symptom of the bacterial disorder or to delay onset of at least one symptom of the bacterial disorder).

As used herein, an amount of a compound effective to treat a bacterial disorder, or a "therapeutically effective amount" refers to an amount of the compound which is effective, upon single or multiple dose administration to a subject, in treating a cell, or in curing, alleviating, relieving or improving a subject with a disorder beyond that expected in the absence of such treatment.

As used herein, an amount of a compound effective to inhibit a bacterial disorder, or "a prophylactically effective amount" of the compound refers to an amount effective, upon single- or multiple-dose administration to the subject, in inhibiting or delaying the occurrence of the onset or recurrence of a disorder or a symptom of the disorder.

As used herein, primary contact means that an individual is in direct physical contact with the subject, e.g., an animal, or that they exchange bodily fluids, e.g., by drinking from the same cup. Secondary contact means that a first individual has primary contact with a second individual and the second individual has direct contact with the subject, e.g., an animal.

As used herein, a "minimum inhibitory concentration (MIC)" is the lowest concentration of an antibacterial that inhibits the visible growth of a bacterium after overnight incubation. MIC can be used to confirm resistance of bacteria to an antibacterial agent and also to monitor the activity of new antibacterial agents. MIC can be determined by agar or broth dilution methods usually following the guidelines of a reference body such as the Clinical and Laboratory Standards Institute (CLSI), British Society for Antimicrobial Chemotherapy (BSAC) or The European Committee on Antimicrobial Susceptibility Testing (EUCAST). Methods to determine MIC are described, e.g., in Andrews J M. *Journal of Antimicrobial Chemotherapy* 48 (Suppl. 1):5-16, (2001).

As used herein, "administered in combination" or a combined administration of two agents means that two or more agents (e.g., compounds described herein) are administered to a subject at the same time or within an interval such that there is overlap of an effect of each agent on the patient. Preferably they are administered within 60, 15, 10, 5, or 1 minute of one another. Preferably the administrations of the agents are spaced sufficiently close together such that a combinatorial (e.g., a synergistic) effect is achieved. The agents can be administered simultaneously, for example in a combined unit dose (providing simultaneous delivery of both agents). Alternatively, the agents can be administered at a specified time interval, for example, an interval of minutes, hours, days or weeks. Generally, the agents are concurrently bioavailable, e.g., detectable, in the subject.

In a preferred embodiment, the agents are administered essentially simultaneously, for example two unit dosages administered at the same time, or a combined unit dosage of the two agents. In another preferred embodiment, the agents are delivered in separate unit dosages. The agents can be administered in any order, or as one or more preparations that includes two or more agents. In a preferred embodiment, at least one administration of one of the agents, e.g., the first agent, is made within minutes, one, two, three, or four hours, or even within one or two days of the other agent, e.g., the second agent. In some cases, combinations can achieve synergistic results, e.g., greater than additive results, e.g., at least 20, 50, 70, 100 or 1000% greater than additive.

As used herein, a "minimum inhibitory concentration (MIC)" is the lowest concentration of an antibacterial that inhibits the visible growth of a bacterium after overnight incubation. MIC can be used to confirm resistance of bacteria to an antibacterial agent and also to monitor the activity of new antibacterial agents. MIC can be determined by agar or broth dilution methods usually following the guidelines of a reference body such as the Clinical and Laboratory Standards Institute (CLSI), British Society for Antimicrobial Chemotherapy (BSAC) or The European Committee on Antimicrobial Susceptibility Testing (EUCAST). Methods to determine MIC are described, e.g., in Andrews J M. *Journal of Antimicrobial Chemotherapy* 48 (Suppl. 1):5-16, (2001).

The term "synergy" or "synergistic" as used herein, refers to an outcome when two agents are used in combination, wherein the combination of the agents acts so as to require a smaller amount of each individual agent than that agent would require alone to be efficacious. For example, the fractional inhibitory concentration (FIC) is one type of measure of the interaction of two agents, such as an anti-bacterial agent and a chitosan derivative, used together, and is a powerful indicator of synergy. FIC uses the minimum inhibitory concentrations (MIC's) of each of the independent agents, A and B, for a particular bacterium as the basis, MIC(A) and MIC(B). Then takes the concentration of each component in a mixture where an MIC is observed, so for a two component system of A and B, MIC (A in B) is the concentration of A in the compound mixture and MIC (B in A) is the concentration of B in the mixture.

The FIC is defined as follows:

$$FIC=MIC(A \text{ in } B)/MIC(A)+MIC(B \text{ in } A)/MIC(B)$$

If FIC< or =0.5, the mixture is synergistic

If FIC=1, the mixture is additive

If FIC>4 the mixture is antagonistic

For example say A=chitosan-arginine and B=ciprofloxacin

Against *Pseudomonas aeruginosa,*

Alone MIC(A)=8 μg/ml

MIC(B)=0.5 μg/ml

For Example 1:

A combination of 1 μg/ml A with 0.1 μg/ml of B, resulting in the killing of bacteria FIC=⅛+0.1/0.5=0.325, and is considered synergistic For Example 2:

Note that if half and half are used, it is additive, for example

A combination of 4 μg/ml A with 0.25 μg/ml of B, resulting in the killing of bacteria FIC=4/8+0.25/0.5=0.5+0.5=1.

In some embodiments the combination results in a reduction in Minimum Inhibitory Concentration (MIC) of the chitosan derivative of at least about 5% (e.g., at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, or at least about 99.5%. In some embodiments the combination results in a reduction in MIC of the anti-bacterial agent of at least about 5% (e.g., at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, at least about 99.5%, at least about 99.9%, at least about 99.99%, or at least about 99.999%.

In some embodiments the combination results in a Fractional Inhibitory Concentration (FIC) of the chitosan derivative and the anti-bacterial agent less than about 0.5 (e.g., less than about 0.4, less than about 0.3, less than about 0.2, less than about 0.1, less than about 0.05, less than about 0.02, less than about 0.01, less than about 0.005, less than about 0.001)

In some embodiments, the combination results in a bactericidal activity at least about 2, 2.5, 3, 3.5, 4, 4.5, or 5 logs more effective than the most effective individual activity, e.g., the activity of the chitosan derivative or the anti-bacterial agent.

For instances where bactericidal activity, rather than inhibitory activity is measured, a time kill assay is used. A minimum bactericida concentration (MBC) can be determined for a given paeriod of time, and with a cut off of 3 or 4 or 5 log reduction in viable bacteria. For the purposes of defining synergy in a time kill assay, acombination of treatments is considered synergistic if the resultant bactericidal activity is 2 logs more effective than the most effective individual activity. [Stratton, C. W. & Cooksey, R. C. (1991). Susceptibility tests: special tests. In *Manual of Clinical Microbiology* (Balows, A., Ed.), pp. 1153-65. American Society Microbiology, Washington D.C.]

Subjects

The subjects described herein include animal subjects. Suitable animal subjects include, but are not limited to, pet, wild, zoo, laboratory, and farm animals. Suitable animal subjects include primates, rodents, and birds. Examples of said animals include, but are not limited to, guinea pigs, hamsters, gerbils, rat, mice, rabbits, dogs, cats, horses, pigs, sheep, cows, goats, deer, rhesus monkeys, monkeys, tamarinds, apes, baboons, gorillas, chimpanzees, orangutans, gibbons, fowl, e.g., pheasant, quail (or other gamebirds), a waterfowl, ostriches, chickens, turkeys, ducks, and geese or free flying bird.

Exemplary disorders in animals include those described above, for example as caused by an infection with a bacteria described above.

Soluble Chitosans and Chitosan Derivatives

Compounds and compositions containing a soluble chitosan or a functionalized chitosan derivative for treating or preventing bacterial infections or generally optimize animal health, e.g., to optimize weight gain to allow for the use of lower doses of anti-bacterial agents, are described herein. These compounds and compositions can be administered to a subject using the methods described herein, for example by administering in a composition described herein.

Chitosan is an insoluble polymer derived from chitin, which is a polymer of N-acetylglucosamine. It is the main component of the exoskeletons of crustaceans (e.g. shrimp, crab, lobster). Chitosan is formed from chitin by deacetylation, and thus is a random copolymer of glucosamine and N-acetylglucosamine monomers. Chitosan is therefore not a single polymeric molecule, but a class of molecules having various molecular weights and various degrees of deacetylation. The degree of deacetylation determines the relative content of free amino groups to total monomers in the chitosan polymer. The percent deacetylation in commercial chitosans is typically between 50-100%. Chitosans with any degree of deacetylation (DDA) greater than 50% are used in the present invention. Methods that can be used for determination of the degree of deacetylation of chitosan include, e.g., ninhydrin test, linear potentiometric titration, near-infrared spectroscopy, nuclear magnetic resonance spectroscopy, hydrogen bromide titrimetry, infrared spectroscopy, and first derivative UV-spectrophotometry. Preferably, the degree of deacetylation of a soluble chitosan or a derivatized chitosan described herein is determined by quantitative infrared spectroscopy.

The chitosan derivatives described herein are generated by functionalizing the resulting free amino groups with positively charged or neutral moieties, as described herein. Chitosans with functionalization between 2% and 50% of the available amines are used in the present invention. Percent functionalization is determined as the % of derivatized amines relative to the total number of available amino moieties prior to reaction on the chitosan polymer. Preferably, the percent functionalization of a derivatized chitosan described herein is determined by H-NMR or quantitative elemental analysis.

The degrees of deacetylation and functionalization impart a specific charge density to the functionalized chitosan derivative. The resulting charge density affects solubility, and the strength of interaction with bacterial cell walls and membranes. The molecular weight is also an important factor in the tenacity of bacterial wall interaction and thus bactericidal activity. Thus, in accordance with the present invention, the degree of deacetylation, the functionalization and the molecular weight must be optimized for optimal efficacy.

The derivatized chitosans described herein have a number of properties which are advantageous including solubility at physiologic pH and antimicrobial activity when in solution or dry at any pH less than about 9. Exemplary chitosan derivatives are described in Baker et al; Ser. No. 11/657,382 filed on Jan. 24, 2007, which is incorporated herein by reference.

A soluble chitosan as described herein, refers to a water soluble chitosan that is not derivatized, specifically on the hydroxyl or amine moieties. Generally a water soluble chitosan has a molecular weight of less than or equal to about 10 kDa and a degree of deacetylation equal or greater than 80%. Water soluble is defined as being fully dissolvable in water at pH 7.

The chitosan derivatives described herein have a range of polydispersity index (PDI) between about 1.0 to about 2.5. As used herein, the polydispersity index (PDI), is a measure of the distribution of molecular weights in a given polymer sample. The PDI calculated is the weight averaged molecular weight divided by the number averaged molecular weight. This calculation indicates the distribution of individual molecular weights in a batch of polymers. The PDI has a value always greater than 1, but as the polymer chains approach uniform chain length, the PDI approaches unity (1). The PDI of a polymer derived from a natural source depends on the natural source (e.g. chitin or chitosan from crab vs. shrimp vs. fungi) and can be affected by a variety of reaction, production, processing, handling, storage and purifying conditions. Methods to determine the polydispersity include, e.g., gel permeation chromatography (also known as size exclusion chromatography); light scattering measurements; and direct calculation from MALDI or from electrospray mass spectrometry. Preferably, the PDI of a soluble chitosan or a derivatized chitosan described herein is determined by HPLC and multi angle light scattering methods.

The chitosan derivatives described herein have a range of molecular weights that are soluble at neutral and physiological pH, and include for the purposes of this invention molecular weights ranging from 5-1,000 kDa. Embodiments described herein feature moderate molecular weights of derivatized chitosans (25 kDa, e.g., from about 15 to about 300 kDa) which can have clumping, diffusible and biofilm disruption properties.

The functionalized chitosan derivatives described herein include the following:

(A) Chitosan-arginine compounds;

(B) Chitosan-natural amino acid derivative compounds;

(C) Chitosan-unnatural amino acid compounds;

(D) Chitosan-acid amine compounds;

(E) Chitosan-guanidine compounds; and (F) Neutral chitosan derivative compounds.

(A) Chitosan-arginine Compounds

In some embodiments, the present invention is directed to chitosan-arginine compounds, where the arginine is bound through a peptide (amide) bond via its carbonyl to the primary amine on the glucosamines of chitosan:

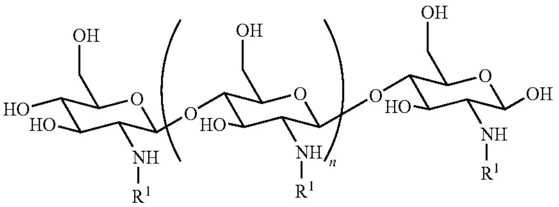

wherein each $R^1$ is independently selected from hydrogen, acetyl, and a group of the following formula:

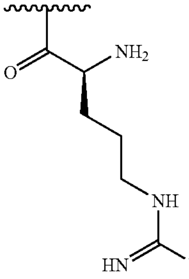

and

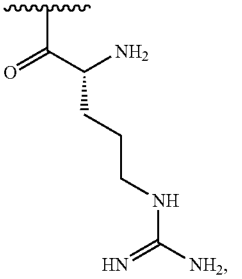

or a racemic mixture thereof, wherein at least 25% of $R^1$ substituents are H, at least 1% are acetyl, and at least 2% are a group of the formula shown above.

(B) Chitosan-Natural Amino Acid Derivative Compounds

In some embodiments, the present invention is directed to chitosan-natural amino acid derivative compounds, wherein the natural amino acid may be histidine or lysine. The amino is bound through a peptide (amide) bond via its carbonyl to the primary amine on the glucosamines of chitosan:

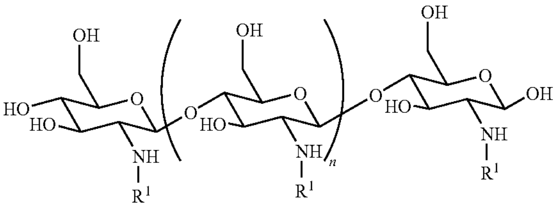

wherein each $R^1$ is independently selected from hydrogen, acetyl, and a group of the following formula:

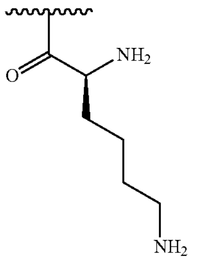

and

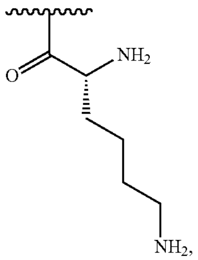

or a racemic mixture thereof, wherein at least 25% of $R^1$ substituents are H, at least 1% are acetyl, and at least 2% are a group of the formula shown above; OR a group of the following formula:

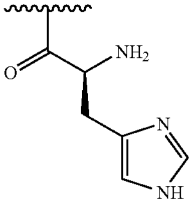

and

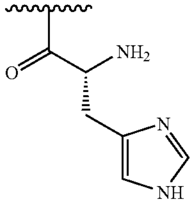

, or a racemic mixture thereof, wherein at least 25% of $R^1$ substituents are H, at least 1% are acetyl, and at least 2% are a group of the formula shown above.

(C) Chitosan-Unnatural Amino Acid Compounds

In some embodiments, the present invention is directed to chitosan-unnatural amino acid compounds, where the unnatural amino acid is bound through a peptide (amide) bond via its carbonyl to the primary amine on the glucosamines of chitosan:

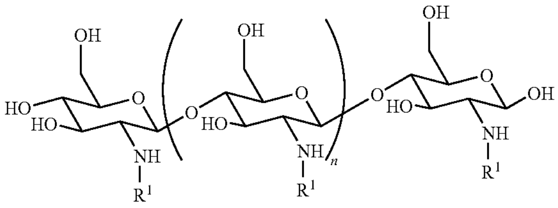

wherein each $R^1$ is independently selected from hydrogen, acetyl, and a group of the following formula:

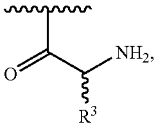

wherein $R^3$ is an unnatural amino acid side chain, and wherein at least 25% of $R^1$ substituents are H, at least 1% are acetyl, and at least 2% are a group of the formula shown above.

Unnatural amino acids are those with side chains not normally found in biological systems, such as ornithine (2,5-diaminopentanoic acid). Any unnatural amino acid may be used in accordance with the invention. In some embodiments, the unnatural amino acids coupled to chitosan have the following formulae:

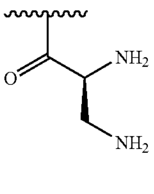

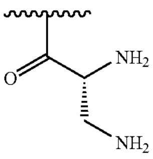

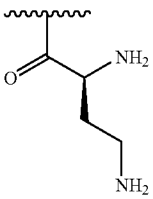

-continued

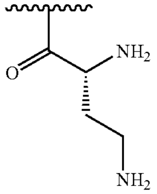
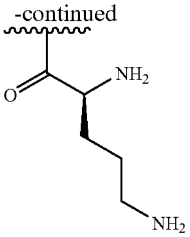
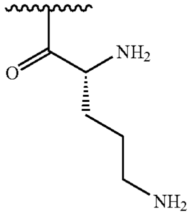
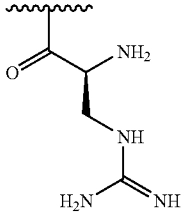
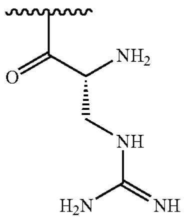
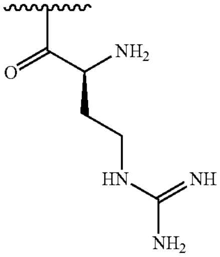
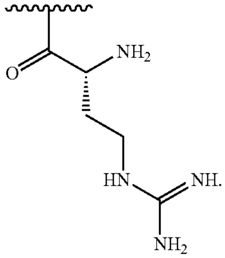

(D) Chitosan-Acid Amine and Guanidine Compounds

In some embodiments, the present invention is directed to chitosan-acid amine compounds, or their guanidylated counterparts. The acid amine is bound through a peptide (amide) bond via its carbonyl to the primary amine on the glucosamines of chitosan:

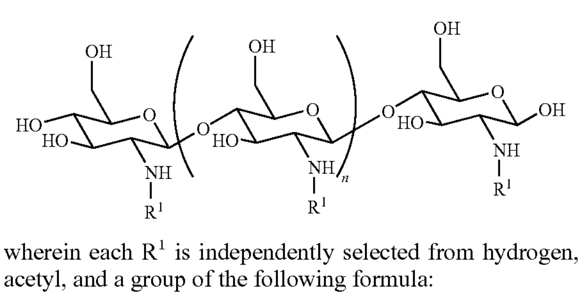

wherein each $R^1$ is independently selected from hydrogen, acetyl, and a group of the following formula:

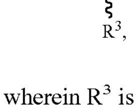

wherein $R^3$ is selected from amino, guanidino, and $C_1$-$C_6$ alkyl substituted with an amino or a guanidino group, wherein at least 25% of $R^1$ substituents are H, at least 1% are acetyl, and at least 2% are a group of the formula shown above In some embodiments, $R^1$ is selected from one of the following:

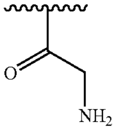
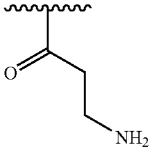
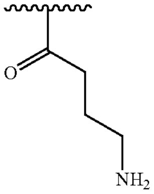
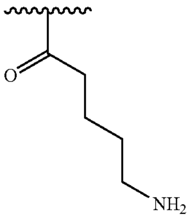
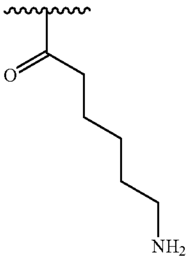
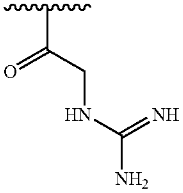
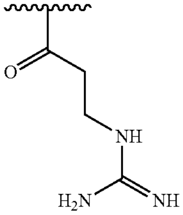
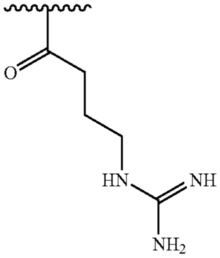
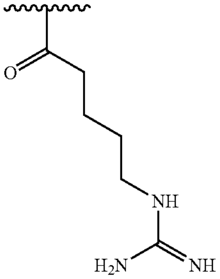
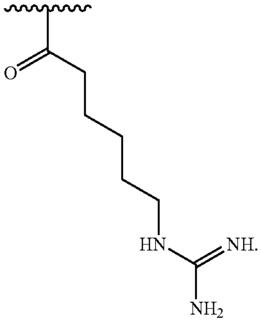

(E) Chitosan-Guanidine Compounds

In some embodiments, the present invention is directed to chitosan-guanidine compounds.

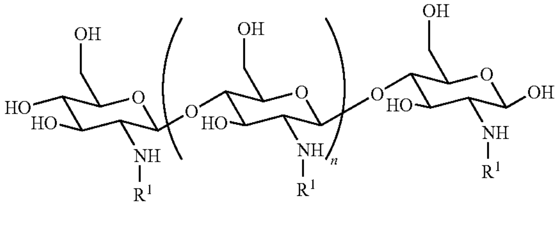

wherein each $R^1$ is independently selected from hydrogen, acetyl, and a group in which $R^1$, together with the nitrogen to which it is attached, forms a guanidine moiety; wherein at least 25% of $R^1$ substituents are H, at least 1% are acetyl, and at least 2% form a guanidine moiety together with the nitrogen to which it is attached.

(F) Neutral Chitosan Derivative Compounds

In some embodiments, the present invention is directed to neutral chitosan derivative compounds. Exemplary neutral chitosan derivative compounds include those where one or more amine nitrogens of the chitosan has been covalently attached to a neutral moiety such as a sugar:

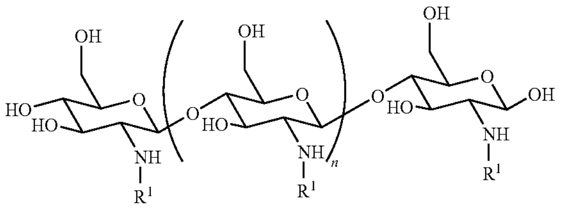

wherein each $R^1$ is independently selected from hydrogen, acetyl, and a sugar (e.g., a naturally occurring or modified sugar) or an a-hydroxy acid. Sugars can be monosaccharides, disaccharides or polysaccharides such as glucose, mannose, lactose, maltose, cellobiose, sucrose, amylose, glycogen, cellulose, gluconate, or pyruvate. Sugars can be covalently attached via a spacer or via the carboxylic acid, ketone or aldehyde group of the terminal sugar. Examples of $\alpha$-hydroxy acids include glycolic acid, lactic acid, and citric acid. In some preferred embodiments, the neutral chitosan derivative is chitosan-lactobionic acid compound or chitosan-glycolic acid compound. Exemplary salts and coderivatives include those known in the art, for example, those described in US 20070281904, the contents of which is incorporated by reference in its entirety.

Compositions

The compounds described herein can be formulated in a variety of manners, including for oral, topical, or inhaled (e.g., orally, enterally, by inhalation spray, nebulizer, topically, rectally, nasally, buccally). The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form.

The compounds and compositions can also be formulated for inclusion in feed or water, or administration by inhalation is particularly desirable for use with animals. For example, in some embodiments, animal feed composition is provided which comprises the chitosan derivatives of the present invention. The derivatized chitosan can be added to animal feed to promote growth and/or prevent infection.

The chitosan derivatives of the present invention are also useful as additives for animal/feed. The chitosan derivative can be formulated in an animal feed premix or animal feed supplement containing the anti-bacterial agent and an edible carrier or diluent. These premixes or animal feed supplements may then be mixed with a sufficient quantity of an appropriate animal feed (e.g., livestock, poultry, fish, pet and/or other animal feed) to provide a final animal feed formulation having the desired level of the chitosan derivative in the feed.

The chitosan derivatives of the present invention are also useful as additives in water. The chitosan derivative can be dissolved and delivered in ad libitum water and supplemented with the soluble anti-bacterial agent. These soluble formulations can provide ease of use, no premixing with the feed-preparing organization and immediate administration based on need.

The compounds of this invention may be administered by aerosol, nebulizer, or inhalation. In some embodiments, the composition is in the form of a dry powder, a suspension, or a solution. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. Exemplary methods and devices for aerosol or inhalation include those described in U.S. Pat. No. 6,962,151, which is incorporated herein by reference in its entirety.

Compositions formulated for inhaled delivery generally include particles having a mean diameter of from about 0.1 μm to about 50 μm (e.g., from about 0.1 μm to about 10 μm, or from about 0.2 μm to about 5 μm. In some embodiments, the composition includes a dispersion of suitably-sized dry particles, for example, precipitants or crystals) or a dispersion of a solution (e.g., droplets) of a suitable size.

Anti-Bacterial Agents

In some embodiments, a chitosan derivative described herein is administered to a subject in combination with an anti-bacterial agent. In some embodiments, the chitosan and anti-bacterial agent act synergistically when administered to the subject (e.g., when fed to the subject).

Anti-bacterial agent action generally falls within one of four mechanisms. Three involve the inhibition or regulation of enzymes involved in cell wall biosynthesis, nucleic acid metabolism and repair, or protein synthesis. The fourth mechanism involves the disruption of membrane structure, like a pore-former. A common example of a pore-former is polymixin B.

General Classes of Anti-Bacterial Agents and Mechanism (a Star Indicates the Anti-Bacterial Agent has been Tested and Shows Synergy)

Aminoglycosides: Inhibit protein synthesis by binding to a portion of the bacterial ribosome. Most of them are bacteriocidal (i.e., cause bacterial cell death).

Bacitracin: Inhibits cell wall production by blocking the step in the process (recycling of the membrane lipid carrier) which is needed to add on new cell wall subunits.

Beta-lactam antibiotics: Antibiotics in this group contain a specific chemical structure (i.e., a beta-lactam ring). This includes penicillins, cephalosporins, carbapenems and monobactams. They inhibit the synthesis of the peptidoglycan layer of bacterial cell walls of Gram positive organisms, by binding to penicillin binding protein (PBP), which is the last step in cell wall synthesis. Although, some Gram negative bacteria seem to be susceptible.

Cephalosporins: These are similar to penicillins in their mode of action but they treat a broader range of bacterial infections. They have structural similarities to penicillins and many people with allergies to penicillins also have allergic reactions to cephalosporins.

Chloramphenicol: Inhibits protein synthesis by binding to a subunit of bacterial ribosomes (50S).

Glycopeptides (e.g., vancomycin): Interferes with cell wall development by blocking the attachment of new cell wall subunits (muramyl pentapeptides).

Macrolides (e.g., erythromycin) and Lincosamides (e.g., clindamycin): Inhibit protein synthesis by binding to a subunit of the bacterial ribosome (50S).

Penicillins: Inhibits formation of the bacterial cell wall by blocking cross-linking of the cell wall structure. The cell wall is a needed protective casing for the bacterial cell.

Quinolones: Blocks DNA synthesis by inhibiting one of the enzymes (DNA gyrase) needed in this process. (Ciprofloxacin is a fluoroquinolone)

Rifampin: Inhibits RNA synthesis by inhibiting one of the enzymes (DNA-dependent RNA polymerase) needed in this process. RNA is needed to make proteins.

Glycopeptide: Like vancoymcin, inhibits cell wall synthesis.

Tetracyclines: Inhibit protein synthesis by binding to the subunit of the bacterial ribosome (30S subunit).

Trimethoprim and Sulfonamides: Blocks cell metabolism by inhibiting enzymes which are needed in the biosynthesis of folic acid which is a necessary cell compound.

Exemplary anti-bacterial agents are provided as follows. Exemplary aminoglycosides include Streptomycin, Neomycin, Framycetin, Parpmycin, Ribostamycin, Kanamycin, Amikacin, Dibekacin, Tobramycin, Hygromycin B, Spectinomycin, Gentamicin, Netilmicin, Sisomicin, Isepamicin, Verdamicin, Amikin, Garamycin, Kantrex, Netromycin, Nebcin, and Humatin. Exemplary carbacephems include Loracarbef (Lorabid). Exemplary carbapenems include Ertapenem, Invanz, Doripenem, Finibax, Imipenem/Cilastatin, Primaxin, Meropenem, and Merrem. Exemplary cephalosporins include Cefadroxil, Durisef, Cefazolin, Ancef, Cefalotin, Cefalothin, Keflin, Cefalexin, Keflex, Cefaclor, Ceclor, Cefamandole, Mandole, Cefoxitin, Mefoxin, Cefprozill, Cefzil, Cefuroxime, Ceftin, Zinnat, Cefixime, Suprax, Cefdinir, Omnicef, Cefditoren, Spectracef, Cefoperazone, Cefobid, Cefotaxime, Claforan, Cefpodoxime, Fortaz, Ceftibuten, Cedax, Ceftizoxime, Ceftriaxone, Rocephin, Cefepime, Maxipime, and Ceftrobriprole. Exemplary glycopeptides include Dalbavancin, Oritavancin, Teicoplanin, Vancomycin, and Vancocin. Exemplary macrolides include Azithromycin, Sithromax, Sumamed, Zitrocin, Clarithromycin, Biaxin, Dirithromycin, Erythromycin, Erythocin, Erythroped, Roxithromycin, Troleandomycin, Telithromycin, Ketek, and Spectinomycin. Exemplary monobactams include Aztreonam. Exemplary penicillins include Amoxicillin, Novamox, Aoxil, Ampicillin, Azlocillin, Carbenicillin, Coxacillin, Diloxacillin, Flucloxacillin Floxapen, Mezlocillin, Methicillin, Nafcillin, Oxacillin, Penicillin, and Ticarcillin. Exemplary polypeptides include Bacitracin, Colistin, and Polymyxin B. Exemplary quinolones include Ciprofloxacin, Cipro, Ciproxin, Ciprobay, Enoxacin, Gatifloxacin, Tequin, Levofloxacin, Levaquin, Lomefloxacin, Moxifloxacin, Avelox, Norfloxacin, Noroxin, Ofloxacin, Ocuflox, Trovafloxacin, and Trovan. Exemplary sulfonamides include Mefenide, Prontosil (archaic), Sulfacetamide, Sulfamethizole, Sulfanilamide (archaic), Sulfasalazine, Sulfisoxazole, Trimethoprim, Trimethoprim-Sulfamethoxazole (co-trimoxazole), and Bactrim. Exemplary tetracyclines include Demeclocyline, Doxycycline, Vibramycin, Minocycline, Minocin, Oxytetracycline, Terracin, Tetracycline, and Sumycin. Other exemplary antibiotics include Salvarsan, Chloamphenicol, Chloromycetin, Clindamycin, Cleocin, Linomycin, Ethambutol, Fosfomycin, Fusidic Acid, Fucidin, Furazolidone, Isoniazid, Linezolid, Zyvox, Metronidazole, Flagyl, Mupirocin, Bactroban, Nitrofurantion, Macrodantin, Macrobid, Platensimycin, Pyrazinamide, Quinupristin/Dalfopristin (Syncerid), Rifampin (rifampicin), and Tinidazole.

Pathogens

As described herein, the compounds and compositions described herein can be administered to a subject to inhibit the growth of bacteria or reduce bacterial load in a subject. Exemplary Gram-negative bacterial pathogens include, e.g., *Escherichia coli, Pseudomonas aeurginosa, Pasteurella multicida, Klebsiella pneumonia, Shigella flexneri, Salmonella* (such as *pullorum* and *gallinarum*), and *Proteus mirabilis*. Exemplary Gram-positive bacterial pathogens include, e.g., *Bacillus subtilis, Staphylococcus aureus Staphylococci, Streptococcus, Clostridium perfringens, Erysipelas insidiosa*, or *Enterococcus* (e.g., vancomycin resistant).

Other exemplary pathogens include: bacteria such as *Streptococcus pneumoniae, Enterococcus faecalis, Enterococcus faecium, Enterobacter* sps., *Proteus* sps., *Serratia marcesens*, Coag. Neg. Staph, *Haemophilus influenzae, Bacillus anthracis, Mycoplasma pneumoniae, Moraxella catarralis, Chlamydia pneumoniae, Legionella pneumophila, Mycobacterium tuberculosis, Helicobacter pylori.*

Other exemplary pathogens also include bacteria that cause resistant bacterial infections such as Methicillin resistant *Staphylococcus aureus*, Mupirocin resistant *Staphylococcus aureus*, Mupirocin and Methicillin resistant *Staphylococcus aureus*, Fluoroquinolone resistant *Staphylococcus aureus*, Vancomycin intermediate resistant *Staphylococcus aureus*, Linezolid resistant *Staphylococcus aureus*, Penicillin resistant *Streptococcus pneumoniae*, Macrolide resistant *Streptococcus pneumoniae*, Fluoroquinolone resistant *Streptococcus pneumoniae*. Vancomycin resistant *Enterococcus faecalis*, Linezolid resistant *Enterococcus faecalis*, Fluoroquinolone resistant *Enterococcus faecalis*, Vancomycin resistant *Enterococcus faecium*, Linezolid resistant *Enterococcus faecium*. Fluoroquinolone resistant *Enterococcus faecium*, Ampicillin resistant *Enterococcus faecium*, Macrolide resistant *Haemophilus influenzae*, β-lactam resistant *Haemophilus influenzae*, Fluoroquinolone resistant *Haemophilus influenzae*, β-lactam resistant *Moraxella catarrhalis*, Methicillin resistant *Staphylococcus epidermidis*, Methicillin resistant *Staphylococcus epidermidis*, Vancomycin resistant *Staphylococcus epidermidis*, Fluoroquinolone resistant *Staphylococcus epidermidis*, Macrolide resistant *Mycoplasma pneumoniae*, Isoniazid resistant *Mycobacterium tuberculosis*, Rifampin resistant *Mycobacterium tuberculosis*, Methicillin resistant coagulase negative *Staphylococci*, Fluoroquinolone resistant coagulase negative *Staphylococci*, Glycopeptide intermediate resistant *Staphylococcus aureus*, Vancomycin resistant *Staphylococcus aureus*, Hetero vancomycin intermediate resistant *Staphylococcus aureus*, Hetero vancomycin resistant *Staphylococcus aureus*, Macrolide-Lincosamide-Streptogramin resistant *Staphylococcus*, β-lactam resistant *Enterococcus faecalis*, β-lactam resistant *Enterococcus faecium*, Ketolide resistant *Streptococcus pneumoniae*, Ketolide resistant *Streptococcus pyogenes*, Macrolide resistant *Streptococcus pyogenes*, Vancomycin resistant *Staphylococcus epidermidis*, multidrug resistant *Clostridium difficile*, multidrug resistant *Acinetibacter baumannii*, multidrug resistant *Kelbsiella pneumoniae*, or multidrug resistant *Escherichia coli.*

Animal Diseases

The compositions and methods described herein can be used, for example to treat or inhibit the onset of an animal disease. Exemplary animal diseases are provided below.

Colibacillosis (Coliform Infections)

Problems attributed to coliform infections are often caused by strains of the *Escherichia coli* organism. There is a marked variation in severity. Problems range from severe acute infections with sudden and high mortality to mild infections of a chronic nature with low morbidity and mortality. Infections may result in a respiratory disease from air sac infection, a septicemic (blood) disease from generalized infections, an enteritis from intestinal infection or a combination of any or all of these conditions. The disease may result from a coliform infection alone as a primary infection, or in combination with other disease agents as a complicating or secondary infection. Secondary infections commonly occur as a part of the classic air sac disease syndrome as a complication with *Mycoplasma gallisepticum* infections.

All ages can be affected; however, the acute septicemia in young turkeys and airsacculitis in young chickens is more common in young growing birds. High, early mortality may occur as the result of navel infections.

The symptoms of this disease are generally caused by *E. coli* bacteria and the toxins produced as they grow and multiply. There are many different strains or serological types within the group of *E. coli* bacteria. Many are normal inhabitants in intestinal tracts of chickens and turkeys and consequently are common organisms in the birds' environments.

*Coccidiosis*

*Coccidiosis* is a disease of fowl caused by a microscopic animal or protozoa and is characterized by diarrhea, unthriftiness and variable levels of mortality. In spite of much research to advance the control and treatment of this disease, it remains the most costly disease of the poultry industry.

*Coccidiosis* is caused by microscopic animals called coccidia. There are many species of coccidia that can infect fowl, domestic animals and humans. Each species of coccidia is host specific and does not infect a wide variety of animals. After an outbreak of a specific species of coccidia, the flock will develop a resistance to the exposed coccidia species but remain resistant to other infective species. This means that a flock may experience several outbreaks of *coccidiosis*, each being caused by a different species of coccidia. Chickens are susceptible to any of nine coccidia species, turkeys are susceptible to seven species and quail are susceptible to at least four different species of coccidia.

*Coccidiosis* is transmitted by direct or indirect contact with droppings of infected birds. When a bird ingests coccidia, the organisms invade the lining of the intestine and produce tissue damage as they undergo reproduction. Within a week after infection, the coccidia shed immature descendants that are referred to as oocysts. The oocysts shed in the droppings are not capable of infecting another bird unless they pass through a maturation process (sporulation) in the litter. This sporulation occurs within a one to three day period if the litter is warm and damp but can take much longer if the conditions are cool and dry. After sporulation the coccidia are infective if consumed by a new host bird.

Fowl Cholera

This disease occurs throughout the country wherever poultry is produced and in recent years has become the most hazardous infectious disease of turkeys. Host range is extensive and includes chickens, turkeys, pheasants, pigeons, waterfowl, sparrows and other free-flying birds.

The causative organism of fowl cholera is *Pasteurella multocida*. The organism can survive at least one month in droppings, three months in decaying carcasses and two to three months in soil. Pasteurella apparently enters tissues of the mouth and upper respiratory tract. The disease is not transmitted through the egg.

Major sources of infection include:

Body excreta of diseased birds that contaminate soil, water, feed, etc.,

Carcasses of birds that have died of the disease,

Contaminated water supplies such as surface tanks, ponds, lakes and streams,

Mechanical transmission by contaminated shoes or equipment.

Studies indicate that animals other than birds may serve as reservoirs of infection and actively spread the disease. These animals include raccoons, opossums, dogs, cats, pigs, and vermin.

Infectious Bronchitis

Infectious bronchitis is an extremely contagious respiratory disease of chickens characterized by coughing, sneezing and rales (rattling). It is caused by a virus that affects chickens only. Other fowl or laboratory animals cannot be infected with this virus. Several distinct strains of the virus exist.

Infectious bronchitis is considered the most contagious of poultry diseases. When it occurs, all susceptible birds on the premises become infected, regardless of sanitary or quarantine precautions. The disease can spread through the air and can "jump" considerable distances during an active outbreak. It can also be spread by mechanical means such as on clothing, poultry crates and equipment. The disease is not egg transmitted and the virus will survive for probably no more than one week in the house when poultry are not present. It is easily destroyed by heat and ordinary disinfectants.

The infection is confined to the respiratory system. Symptoms are difficult breathing, gasping, sneezing and rales. Some birds may have a slight watery nasal discharge. The disease never causes nervous symptoms. It prevails for ten to fourteen days in a flock and symptoms lasting longer than this are from some other cause.

In chickens under three weeks of age, mortality may be as high as thirty or forty percent. The disease does not cause a significant mortality in birds over five weeks of age. Feed consumption decreases sharply and growth is retarded.

Necrotic Enteritis

Necrotic enteritis is an acute disease that produces a marked destruction of the intestinal lining of the digestive tract. Common field names (rot gut, crud and cauliflower gut) accurately describe the condition. The cause of the disease is *Clostridium perfringens*, a spore-forming, rod-shaped bacterium. Bacterial organisms and their toxins are the primary cause but *coccidiosis* may be a contributing factor. Most of the damage to the intestinal lining apparently is due to toxins produced by the bacterial organisms.

Little is known about the spread of the disease but transmission is thought to occur by oral contact with the droppings from infected birds. Necrotic enteritis appears suddenly in the affected flock. Apparently healthy birds may become acutely depressed and die within hours. Mortality is usually between two and ten percent, but may be as high as thirty percent in severe outbreaks. Losses due to reduced growth and feed conversion may be more costly than flock mortality.

Lesions of the disease usually involve the lower half of the small intestine, but in some instances the entire length of the tract is involved. The intestine is dilated, contains dark offensive fluid and a diphtheritic cauliflower-like membrane that involves the mucosa. The lining of the intestine will have a coarse Turkish-towel appearance and portions of the lining may slough off and pass out with the intestinal contents. Diagnosis in based upon history, symptoms and findings of the characteristic lesions.

Bacitracin or Virginiamycin are effective treatments administered in the feed. Bacitracin can also be given in the drinking water. Supportive vitamin treatment may enhance the effectiveness of the treatments. Preventive medication may be of value on premises where prior infections have been observed. Since *coccidiosis* may be a contributing factor, attention must be given to an effective *coccidiosis* control program.

Ulcerative Enteritis (Quail Disease)

Ulcerative enteritis is an acute or chronic infection of game birds, chickens, turkeys and other domestic fowl. Death losses may be high for young quail or pullets being raised for egg production.

The cause of the disease is *Clostridium colinum*, a spore forming bacterial rod. The infection spreads by the droppings from sick or carrier birds to healthy birds. The disease organism is very resistant to disinfectants and will persist under varying environmental conditions.

Bovine Mastitis

Bovine mastitis is an infection and inflammation of the mammary gland that causes mastitis. *Pseudomonas aeruginosa* remains one of the most prevalent infective bacteria, and most resistant to convetional antibiotics. *Escherichia coli* and more commonly *Staphylococus aureus* and *Streptococcus uberis* are a contributing bacterial problems in mastitis.

Salmonellosis

Bovine salmonellosis is often associated with a herd outbreak, and is caused by any number of salmonella serotypes, now classified into a single species *Salmonella enterica*. *Salmonella* infects any animal with a gastrointestinal tract, and is thus important to prevent, or if necessary quarantine and treat immediately.

EXAMPLES

Example 1

Animal Studies—Poultry Study in Feed

Various doses of two different functionalized chitosan-arginines were mixed in feed, both originally 84% degree of deacetylation. "10% functionalized" has a MW of 39 kDa, 12% functionalized, % DDA=82 and polydispersity index (PDI) of 1.5. "30% functionalized" has a MW of 27 kDa, 26% functionalized, % DDA=82 and polydispersity index (PDI) of 1.7. Dosing of feed may be irregular due to challenges in mixing extremely small quantities of material uniformly (sprayed on cornmeal from water solution, mixed with feedmeal). Twelve replicate pens of five chicks were used for each treatment. Treated feed was fed for 8 days, and weight gain and feed conversion were examined after 21 days (comparison with day 1). The results of this study are shown in FIG. 1 and Table 1. Awt21 is the average weight gain after 21 days and P Diff is the statistical P value between the measured and control.

TABLE 1

Poultry study in feed

| Treatment | Dosage (mg/kg) | Awt21 (kg) | P Diff* |
|---|---|---|---|
| Negative control | — | 0.728 | |
| Penicillin | 55 | 0.852 | 0.0001 |
| Chitosan 10% | 5 | 0.764 | 0.07 |
| Chitosan 10% | 25 | 0.768 | 0.04 |
| Chitosan 10% | 100 | 0.747 | 0.35 |
| Chitosan 10% | 500 | 0.769 | 0.09 |
| Chitosan 30% | 5 | 0.739 | 0.60 |
| Chitosan 30% | 10 | 0.774 | 0.03 |
| Chitosan 30% | 50 | 0.751 | 0.25 |

Example 2

Animal Study—Poultry Study in Water

Figure 2:
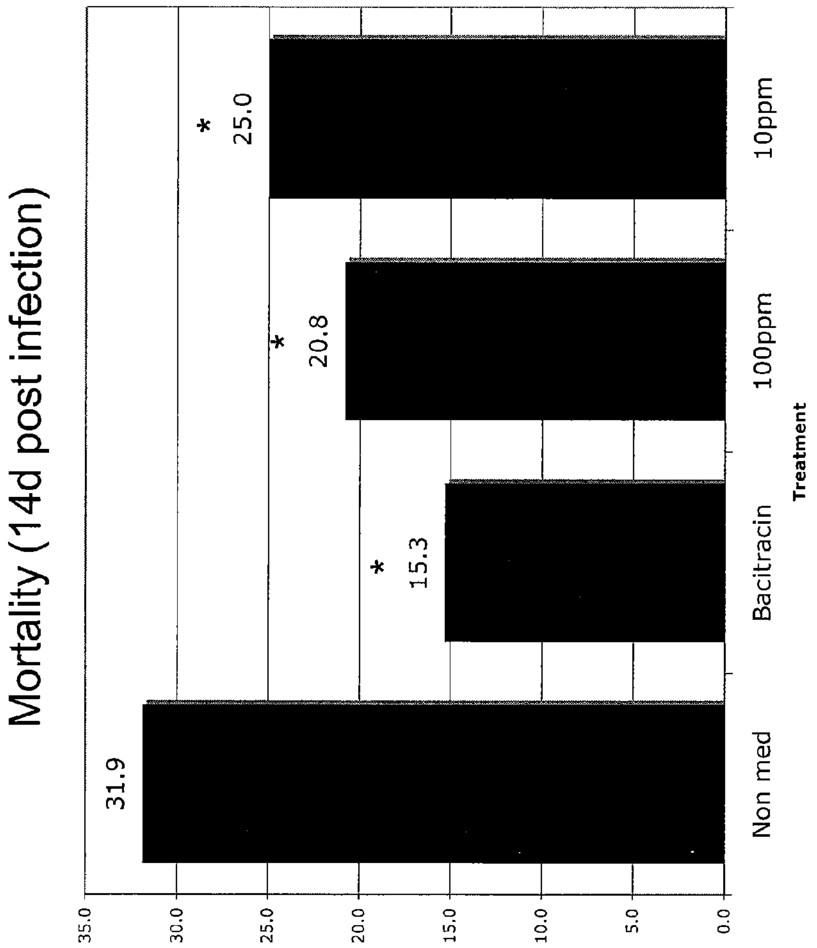
FIG. 2 depicts the effect of chitosan-arginine delivered in water on mortality in poultry study.
Figure 3:
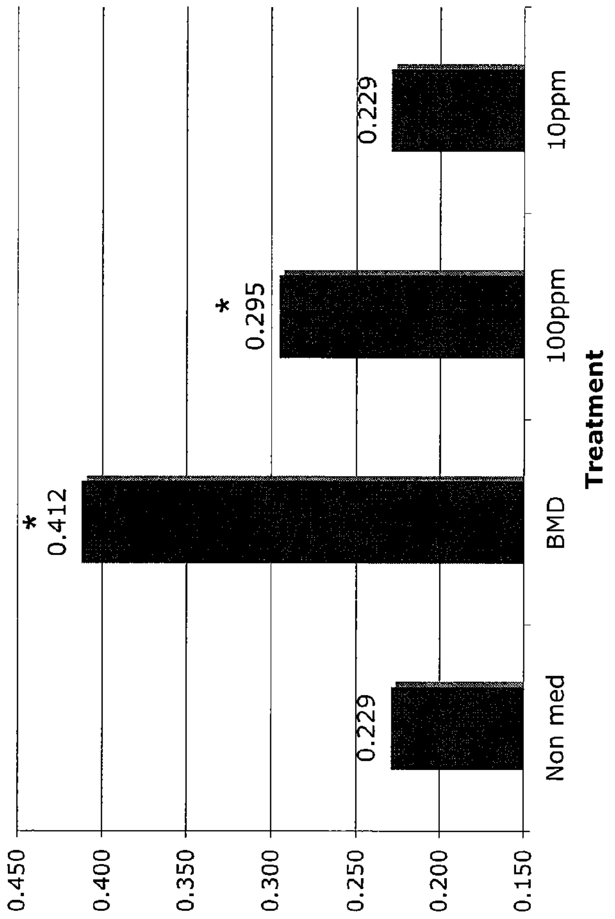
FIG. 3 depicts the effect of chitosan-arginine delivered in water on weight gain in poultry study

A Nectrotic Enteritis model was used in this study. Briefly, animals were infected with 2 cycles of coccidia then with *Clostridium perfringens* via standard procedure as described in references, e.g., C. L. Hofacre, G. F. Mathis, S. H. Miller, and M. W. LaVorgna. 2007. "Use of Bactracin and Roxarsone to Reduce Salmonella Heidelberg Shedding Following a Necrotic Enteritis Challenge Model." *J. Appl. Poult. Res.* 16:275-279. Various doses of chitosan-arginine were given via continuous source in water at 1 day prior to CP infection and for 5 days post infection. Chitosan-arginine used in this study has a MW=22 kDa, 36% functionalized, % DDA=89 and PDI=1.7. Nine pens each of 10 broilers were used for each treatment. Mortality, weight gain (at 8 and 14 days post infection) and feed conversion were examined. The results of this study are shown in FIGS. 2 and 3.

Example 3

Small Subset of Bacteria Important to Poultry

Bacteria were exposed to chitosan-arginine for the time indicated. The bacteria were spun down, rinsed, resuspended and spread on agar plates in order to count the remaining colony forming units (CFU).

Figure 4:
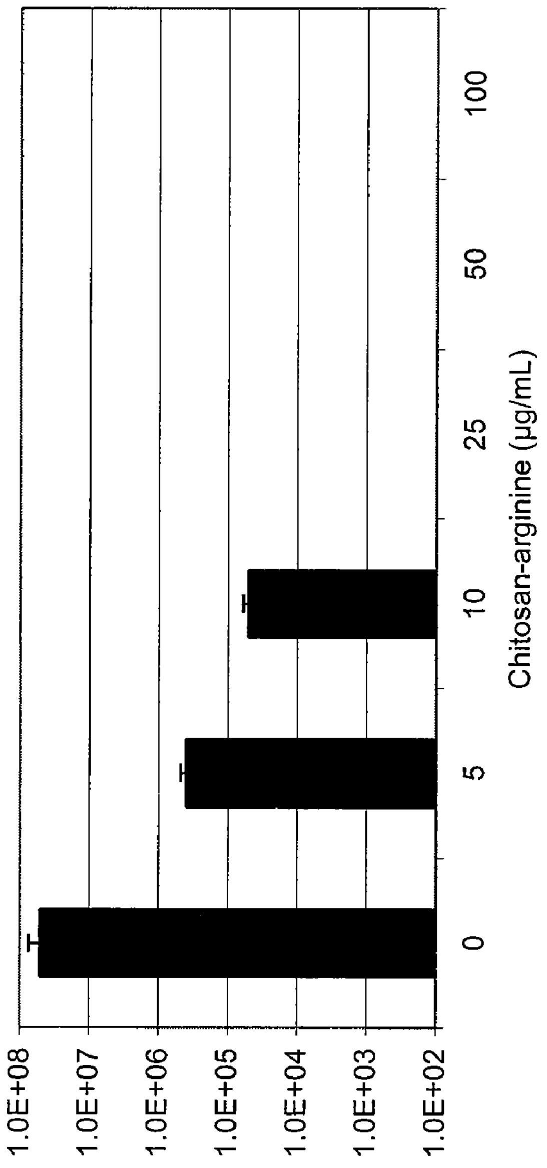
FIG. 4 depicts the inhibitory effect of chitosan-arginine on *Pasteurella multocida*.

*Pasteurella multocida* is a Gram-negative, non-motile coccobacillus that is penicillin-sensitive (most Gram-negative bacteria are not sensitive to Penicillin). *Pasteurella multocida* was treated with chitosan-arginine for 1 hour in water (C/A 37%, 28 kDa). The result is shown in FIG. 4.

Figure 5:
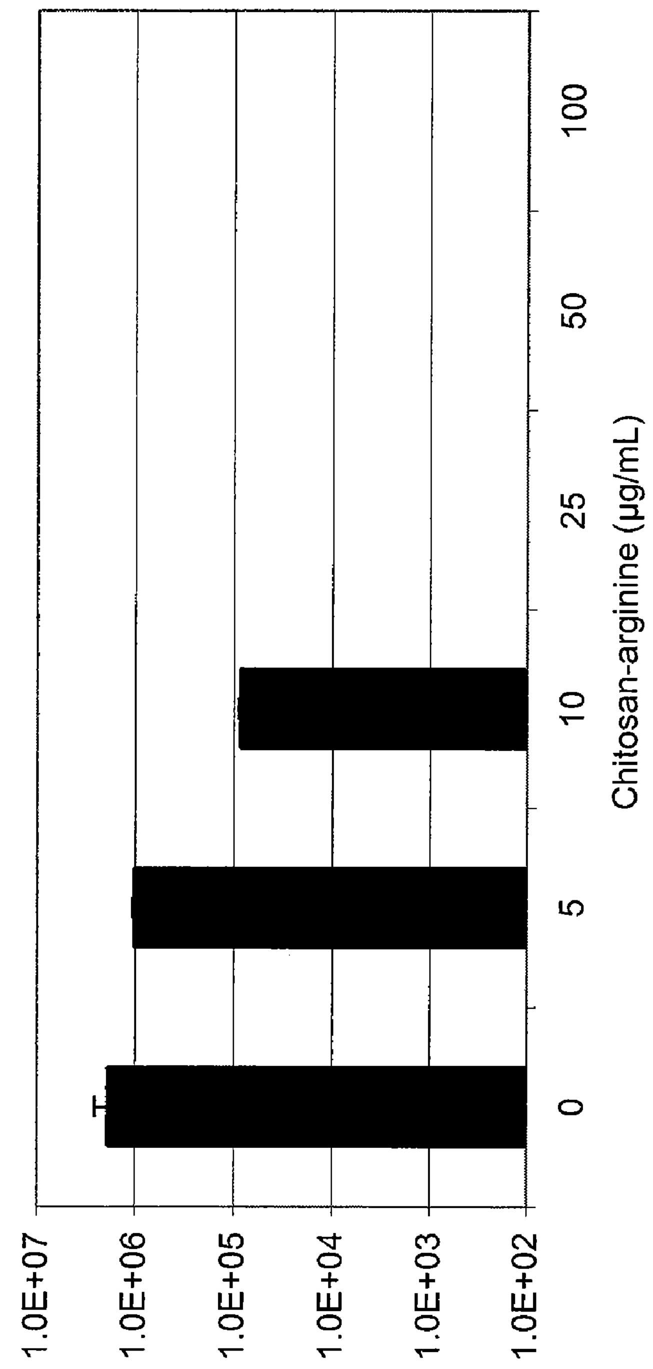
FIG. 5 depicts the inhibitory effect of chitosan-arginine on *E. coli*.

*E. Coli* is a Gram-negative bacterium, often responsible for sacculitis, a secondary infection of the air sac. *E. Coli* was treated with chitosan-arginine for 1 hour in water (C/A 37%, 28 MW). The result is shown in FIG. 5.

Example 4

Synergy in Inhibition of Animal Pathogens

The effect of chitosan-arginine on the inhibition of various species of bacteria which infect animals was evaluated using the method as described above. The results are shown in Table 2.

TABLE 2

Animal bacteria and standard antibiotics shown to exhibit synergy with chitosan-arginine

| | | |
|---|---|---|
| *Pasteurella multocida* | Penicillins, Tetracycline, Virginiamycin | Fowl cholera |
| *Clostridium perfringens* | Bacitracin, Virginiamycin | Necrotic enteridis |
| *Escherichia Coli* | Tetracycline | Sacculitis, colifom infections, enteritis, septiceimia |
| *Salmonella enterica* | Bacitracin | Necrotic enteritis, enteritis |

Example 5

Chitosan-Arginine and Bacitracin Synergy against *S. enterica* (ATCC 700720)

Micro-dilutions were performed for chitosan-arginine (C/A; 25% Functionalization, 43 kDa, 2.28 PDI, 88% DDA) and Bacitracin to cover a range of doses in 96-well plates in a checkerboard assay format. Approximately $10^6$ cells/mL were added to each well. Incubation occurred at ambient temperature for 20 h, then the bacteria were centrifuged and resuspended in an appropriate growth media. The optical density (OD) was read over the course of 18 h at 37° C. The time (in seconds) to an arbitrary threshold OD of 0.15 was used with reference to a growth curve, to calculate the initial bacterial concentration of bacteria (vCFU). Synergy is defined as >2 log decrease in the vCFU with combination treatment at 24 hours compared with that of the more active of each of the two treatments alone.

As shown in Table 3, a synergistic effect was observed when chitosan-arginine (C/A) was used with Bacitracin (BAC) to kill *S. enterica*.

TABLE 3

Chitosan-arginine and Bacitracin synergy against *S. enterica*

| Assay | Treatment (μg/mL) | Total logs recoverable | C/A (log reduction alone) | Bacitracin (log reduction alone) | Total log reduction | Log reduction beyond C/A |
|---|---|---|---|---|---|---|
| 1* | C/A 16 BAC 8 | 8.6 | 4.6 | 0.08 | 5.9 | 1.3 |
| | C/A 8 BAC 8 | 8.6 | 4.4 | 0.08 | 5.6 | 1.2 |
| | C/A 8 BAC 4 | 8.6 | 4.4 | 0.08 | 5.5 | 1.0 |
| 2* | C/A 16 BAC 4 | 7.1 | 3.3 | 0 | 5.4 | 2.1 |
| | C/A 8 BAC 4 | 7.1 | 3.2 | 0 | 5.4 | 2.1 |
| | C/A 16 BAC 2 | 7.1 | 3.3 | 0.2 | 5.1 | 1.9 |
| | C/A 8 BAC 2 | 7.1 | 3.2 | 0.2 | 5.0 | 1.7 |

*C/A 25% Functionalization, 43 kDa, 2.28 PDI, 88% DDA

Example 6

Chitosan-Arginine and Bacitracin Synergy Against *P. multocida* (ATCC 11039)

The experiment was performed as described in Example 5. Synergy is defined as >2 log decrease in the vCFU with combination treatment at 24 hours compared with that of the more active of each of the two treatments alone. In this experiment, chitosan-arginine (C/A) has a bactericidal concentration at 10 μg/mL, and Bacitracin has a bactericidal concentration at >128 μg/mL.

As shown in Table 4, a synergistic effect was observed when chitosan-arginine (C/A) was used with Bacitracin (BAC) to kill *P. multocida* (ATCC 11039).

TABLE 4

Chitosan-arginine and Bacitracin synergy against *P. multocida* (ATCC 11039)

| Assay | Treatment (μg/mL) | Total logs recoverable | C/A (log reduction alone) | Bacitracin (log reduction alone) | Total log reduction | Log reduction beyond C/A |
|---|---|---|---|---|---|---|
| 1* | C/A 4 BAC 32 | 6.6 | 3.3 | 0 | 5.2 | 1.9 |
| 2* | C/A 8 BAC 32 | 6.9 | 4.4 | 0.2 | 6.9 | 2.5 |

*C/A 25% Functionalization, 43 kDa, 2.28 PDI, 88% DDA

Example 7

Chitosan-Arginine and Tetracycline Synergy against *C. perfringens* (ATCC 12919)

The experiment was performed as described in Example 5 except that Tetracycline was used instead of Bacitracin.

Figure 6:
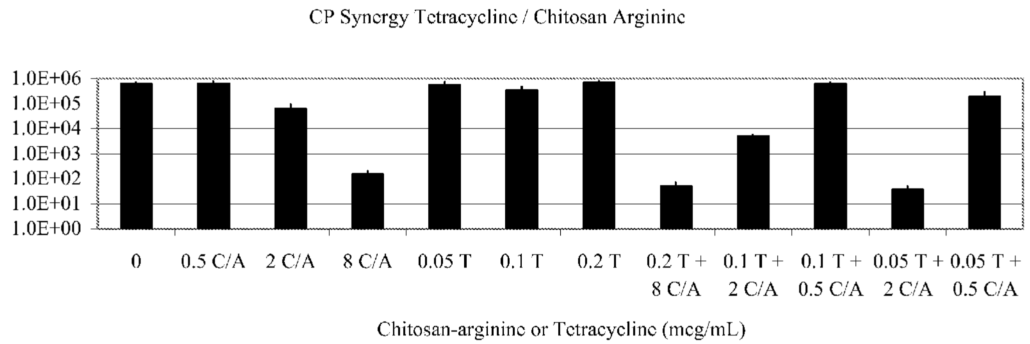
FIG. 6 depicts the chitosan-arginine and tetracycline synergy against *C. perfringens* (ATCC 12919).

As shown in Table 5 and FIG. 6, a synergistic effect was observed when chitosan-arginine (C/A) was used with Tetracycline (TET) to kill *C. perfringens* (ATCC 12919).

TABLE 5

Chitosan-arginine and Tetracycline synergy against *C. perfringens* (ATCC 12919)

| Assay | Treatment (μg/mL) | Total logs recoverable | C/A (log reduction alone) | Tetracycline (log reduction alone) | Total log reduction | Log reduction beyond C/A |
|---|---|---|---|---|---|---|
| 1*1*1* | C/A 2<br>TET 0.05 | 5.8 | 1.3 | 0.1 | 4.5 | 3.2 |
| 2* | C/A 0.5<br>TET 0.2 | 6.7 | 0.3 | 0.1 | 2.7 | 2.4 |
| | C/A 8<br>TET 0.2 | 6.7 | 2.3 | 0.1 | 3.6 | 1.3 |

*C/A 25% Functionalization, 43 kDa, 2.28 PDI, 88% DDA

Other embodiments are within the following claims.

What is claimed is:

1. A method of improving the amount of weight an animal gains for a given amount of feed, comprising:

administering an effective amount of a derivatized chitosan to said animal, of formula (I):

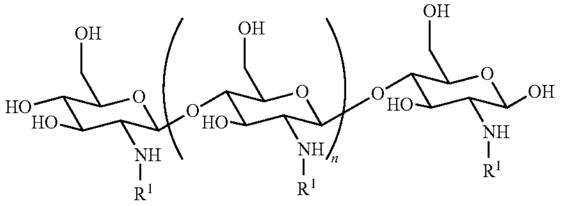

wherein:

n is an integer between 20 and 6000; and each $R^1$ is independently selected for each occurrence from hydrogen, acetyl, and a group of formula (II), wherein formula (II) is selected from:

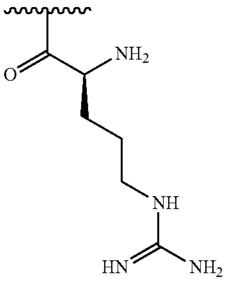

and

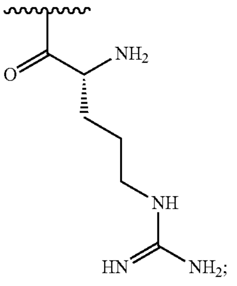

wherein at least 25% of $R^1$ substituents are H, at least 1% of $R^1$ substituents are acetyl, and at least 2% of $R^1$ substituents are a group of formula (II), and further administering to the animal an antibacterial agent, thereby improving the amount of weight an animal gains for a given amount of feed.

2. The method of claim 1, wherein the anti-bacterial agent and derivatized chitosan act synergistically.

3. The method of claim 1, wherein the anti-bacterial agent is present at a concentration, or administered at a dose, which is less than the lowest concentration, or dose, that would improve the amount of weight an animal gains for a given amount of feed in the absence of the derivatized chitosan.

4. The method of claim 1, wherein the anti-bacterial agent is present at a concentration, or administered at a dose, which is less than the lowest concentration, or dose, generally used to improve the amount of weight an animal gains for a given amount of feed.

5. The method of claim 1, wherein the anti-bacterial agent is present at a concentration, or administered at a dose, which is less than 90% of the lowest concentration, or dose, that would improve the amount of weight an animal gains for a given amount of feed in the absence of the derivatized chitosan.

6. The method of claim 1, wherein the anti-bacterial agent is present at a concentration, or administered at a dose, which is less than 90% of the lowest concentration, or dose, generally used to improve the amount of weight an animal gains for a given amount of feed.

7. The method of claim 1, wherein the derivatized chitosan is administered orally.

8. The method of claim 7, wherein the derivatized chitosan is administered in the animal subject's feed or water.

9. The method of claim 1, wherein the molecular weight of the derivatized chitosan is from about 25 to about 100 kDa.

10. The method of claim 1, wherein the derivatized chitosan is administered in a feed preparation.

11. The method of claim 1, wherein the derivatized chitosan is administered in a water preparation.

12. The method of claim 1, wherein the anti-bacterial agent is selected from the group consisting of aminoglycosides, beta-lactam antibiotics, macrolides, antibiotic polypeptides, antibiotic lipopeptides, antibiotic glycopeptides, monobactams, quinolones, sulfonamides and tetracyclines.

13. The method of claim 1, wherein the derivatized chitosan is administered through inhalation.

14. The method of claim 1, wherein the animal subject is also administered a vitamin treatment.

15. The method of claim 1, wherein the derivatized chitosan is administered to the animal subject at 5 to 500 mg/kg weight of animal subject.

* * * * *